United States Patent
Stupp et al.

(10) Patent No.: US 7,851,445 B2
(45) Date of Patent: Dec. 14, 2010

(54) ANGIOGENIC HEPARIN-BINDING EPITOPES, PEPTIDE AMPHIPHILES, SELF-ASSEMBLED COMPOSITIONS AND RELATED METHODS OF USE

(75) Inventors: Samuel I. Stupp, Chicago, IL (US); Kanya Rajangam, Wilmette, IL (US); James F. Hulvat, Chicago, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 11/368,582

(22) Filed: Mar. 6, 2006

(65) Prior Publication Data

US 2007/0277250 A1  Nov. 29, 2007

Related U.S. Application Data

(60) Provisional application No. 60/658,503, filed on Mar. 4, 2005.

(51) Int. Cl.
A61K 38/10 (2006.01)
(52) U.S. Cl. .......................... 514/14; 530/326
(58) Field of Classification Search .............. None
See application file for complete search history.

(56) References Cited

U.S. PATENT DOCUMENTS

| | | | |
|---|---|---|---|
| 4,554,101 A | 11/1985 | Hopp | |
| 4,930,077 A | 5/1990 | Fan | |
| 5,114,713 A | 5/1992 | Sinigaglia | |
| 5,130,123 A | 7/1992 | Reynolds et al. | |
| 5,208,111 A | 5/1993 | Decher et al. | |
| 5,670,483 A | 9/1997 | Zhang et al. | |
| 5,733,868 A | 3/1998 | Peterson et al. | |
| 5,843,780 A | 12/1998 | Thomson | |
| 5,871,767 A | 2/1999 | Dionne et al. | |
| 5,955,343 A | 9/1999 | Holmes et al. | |
| 5,993,541 A | 11/1999 | Litvin et al. | |
| 6,051,272 A | 4/2000 | Stupp et al. | |
| 6,085,206 A | 7/2000 | Domini et al. | |
| 6,096,863 A | 8/2000 | Fields et al. | |
| 6,156,321 A | 12/2000 | Thorpe et al. | |
| 6,181,909 B1 | 1/2001 | Burstein et al. | |
| 6,201,065 B1 | 3/2001 | Pathak et al. | |
| 6,265,539 B1 | 7/2001 | Arlinghaus | |
| 6,269,368 B1 | 7/2001 | Diamond | |
| 6,270,765 B1 | 8/2001 | Deo et al. | |
| 6,309,862 B1 | 10/2001 | Jarekrans et al. | |
| 6,391,297 B1 | 5/2002 | Halvorsen | |
| 6,444,723 B1 | 9/2002 | Kline | |
| 6,458,924 B2 | 10/2002 | Knudsen et al. | |
| 6,473,730 B1 | 10/2002 | McKeown et al. | |
| 6,548,048 B1 | 4/2003 | Cuthbertson et al. | |
| 6,548,630 B1 | 4/2003 | Zhang et al. | |
| 6,562,619 B1 | 5/2003 | Gearhart et al. | |
| 6,800,481 B1 | 10/2004 | Holmes et al. | |
| 6,855,329 B1 | 2/2005 | Shakesheff et al. | |
| 6,890,654 B2 | 5/2005 | Stupp et al. | |
| 7,371,719 B2 | 5/2008 | Stupp et al. | |
| 7,390,526 B2 | 6/2008 | Stupp et al. | |
| 7,534,761 B1 | 5/2009 | Stupp et al. | |
| 7,544,661 B2 | 6/2009 | Stupp et al. | |
| 7,554,021 B2 | 6/2009 | Stupp et al. | |
| 2002/0007217 A1 | 1/2002 | Jacob et al. | |
| 2002/0046018 A1 | 4/2002 | Marcu et al. | |
| 2002/0142277 A1 | 10/2002 | Burstein et al. | |
| 2002/0160471 A1 | 10/2002 | Kisiday et al. | |
| 2003/0050231 A1 | 3/2003 | Rosen et al. | |
| 2003/0059906 A1 | 3/2003 | Hubbell et al. | |
| 2003/0092672 A1 | 5/2003 | Darcy et al. | |
| 2003/0176335 A1 | 9/2003 | Zhang et al. | |
| 2004/0001893 A1 | 1/2004 | Stupp et al. | |
| 2004/0018961 A1 | 1/2004 | Stupp et al. | |
| 2004/0022718 A1 | 2/2004 | Stupp et al. | |
| 2004/0068266 A1 | 4/2004 | Delmotte | |
| 2004/0214272 A1 | 10/2004 | La Rosa et al. | |
| 2004/0258726 A1 | 12/2004 | Stupp et al. | |
| 2005/0208589 A1 | 9/2005 | Stupp et al. | |
| 2005/0209145 A1 | 9/2005 | Stupp et al. | |
| 2005/0214257 A1 | 9/2005 | Zhao et al. | |
| 2005/0272662 A1 | 12/2005 | Stupp et al. | |
| 2006/0149036 A1 | 7/2006 | Stupp et al. | |
| 2006/0188555 A1 | 8/2006 | Cormier et al. | |
| 2006/0247165 A1 | 11/2006 | Stupp et al. | |
| 2008/0175883 A1 | 7/2008 | Hsu et al. | |
| 2008/0248569 A1 | 10/2008 | Mata et al. | |

FOREIGN PATENT DOCUMENTS

| | | |
|---|---|---|
| JP | 03099096 A | 4/1991 |
| WO | 93/22343 A1 | 11/1993 |
| WO | 94/02506 A1 | 2/1994 |

(Continued)

OTHER PUBLICATIONS

Mulloy et al., Glycobiology 2000 v100 pp. 1147-1156.*
UniProt entry for Q899Z6 obtained from http:/www.pir.uniprot.org accessed Mar. 2008, 3 pages.*
Bruggemann et al., PNAS Feb. 4, 2003 v100 pp. 1316-1321.*
Hui (Undergraduate research symposium, 45 pages, retrieved from http://www.northwestern.edu/provost/students/research_symposium/program2004.pdf on Oct. 14, 2009).*
Wayback machine (http://www.archive.org entry, 1 page, for http://www.northwestern.edu/provost/students/research_symposium/program2004.pdf retrieved on Oct. 14, 2009).*
U.S. Appl. No. 11/337,316, filed Jan. 23, 2006, Stupp et al.
Brown, Walter E. Dec. 15, 1962. "Octacalcium Phosphate and Hydroxyapatite." *Nature*. vol. 196, pp. 1048-1050.

(Continued)

*Primary Examiner*—Anish Gupta
*Assistant Examiner*—Ronald T Niebauer

(57) ABSTRACT

Peptide amphiphiles and related compositions comprising sulfated polysaccharides, such as but not limited to sulfated glycosaminoglycans, and methods of use relating to the encapsulation and/or controlled release of angiogenic growth factor(s).

12 Claims, 5 Drawing Sheets

FOREIGN PATENT DOCUMENTS

| WO | 97/14713 A1 | 4/1997 |
|---|---|---|
| WO | 97/20639 A1 | 6/1997 |
| WO | 98/07752 A1 | 2/1998 |
| WO | 99/36107 A1 | 7/1999 |
| WO | 99/55383 A2 | 11/1999 |
| WO | 00/13710 A2 | 3/2000 |
| WO | 00/44808 A1 | 8/2000 |
| WO | WO 00/45831 * | 8/2000 |
| WO | 00/52145 A2 | 9/2000 |
| WO | 00/64481 A1 | 11/2000 |
| WO | 01/00650 A1 | 1/2001 |
| WO | 01/55302 A2 | 8/2001 |
| WO | 02/062969 A2 | 8/2002 |
| WO | 03/040336 A2 | 5/2003 |
| WO | 03/054146 A2 | 7/2003 |
| WO | 03/070749 A2 | 8/2003 |
| WO | 03/084980 A2 | 10/2003 |
| WO | 03/090255 A2 | 10/2003 |
| WO | 2004/003561 A1 | 1/2004 |
| WO | 2004/018628 A2 | 3/2004 |
| WO | 2004/024778 A2 | 3/2004 |
| WO | 2004/046167 A2 | 6/2004 |
| WO | 2004/072104 A2 | 8/2004 |
| WO | 2004/091370 A2 | 10/2004 |
| WO | 2004/106359 A2 | 12/2004 |
| WO | 2005/003292 A2 | 1/2005 |
| WO | 2005/014619 A2 | 2/2005 |
| WO | 2005/056039 A1 | 6/2005 |
| WO | 2005/056576 A2 | 6/2005 |
| WO | 2006/096614 A2 | 9/2006 |

OTHER PUBLICATIONS

Liang, W. Y. and A. D. Yoffe. Jan. 8, 1968. "Transmission Spectra of ZnO Single Crystals." *Physical Review Letters*. vol. 20, No. 2, pp. 59-62.

Greenfield, Norma and Gerald D. Fasman. Oct. 1969. "Computed Circular Dichroism Spectra for the Evaluation of Protein Conformation." *Biochemistry*. vol. 8, No. 10, pp. 4108-4116.

Hantke, Klaus and Volkmar Braun. 1973. "Covalent Binding of Lipid to Protein: Diglyceride and Amide-Linked Fatty Acid at the N-Terminal End of the Murein-Lipoprotein of the *Escherichia coli* Outer Membrane." *Eur. J. Biochem*. vol. 34, No. 2, pp. 284-296.

Balcerski, James S., E. S. Pysh, G. M. Bonora, and C. Toniolo. Jun. 9, 1976. "Vacuum Ultraviolet Circular Dichroism of β-Forming Alkyl Oligopeptides." *Journal of the American Chemical Society*. vol. 98, No. 12, pp. 3470-3473.

Jacobson, Bruce S. and Daniel Branton. Jan. 21, 1977. "Plasma Membrane: Rapid Isolation and Exposure of the Cytoplasmic Surface by Use of Positively Charged Beads." *Science*. vol. 195, No. 4275, pp. 302-304.

Biesecker, G., J. Ieuan Harris, J. C. Thierry, J. E. Walker, and A. J. Wonacott. Mar. 24, 1977. *Nature*. vol. 266, pp. 328-333.

Kelly, Margaret M., E. S. Pysh, G. M. Bonora, and C. Toniolo. May 11, 1977. "Vacuum Ultraviolet Circular Dichroism of Protected Homooligomers Derived from L-Leucine." *Journal of the American Chemical Society*. vol. 99, No. 10, pp. 3264-3266.

Blumenthal, N. C., A. S. Posner, L. D. Silverman, and L. C. Rosenberg. 1979. "Effect of Proteoglycans on in Vitro Hydroxyapatite Formation." *Calcified Tissue International*. vol. 27, No. 1, pp. 75-82.

Richardson, P. M., U. M. McGuinness, and A. J. Aguayo. Mar. 20, 1980. "Axons from CNS Neurones Regenerate into PNS Grafts." *Nature*. vol. 284, pp. 264-265.

Lim, Franklin and Anthony M. Sun. Nov. 21, 1980. "Microencapsulated Islets as Bioartificial Endocrine Pancreas." *Science*. vol. 210, No. 4472, pp. 908-910.

Jain, Rakesh K., Chhitar M. Gupta, and Nitya Anand. 1981. "Synthesis of Peptidylglycophospholipids, Novel Derivatives of Muramyl-Dipeptide." *Tetrahedron Letters*. vol. 22, No. 24, pp. 2317-2320.

Sarin, Virender K., Stephen B. H. Kent, James P. Tam, and R. B. Merrifield. 1981. "Quantitative Monitoring of Solid-Phase Peptide Synthesis by the Ninhydrin Reaction." *Analytical Biochemistry*. vol. 117, pp. 147-157.

Yannas, I. V., J. F. Burke, D. P. Orgill, E. M. Skrabut. Jan. 8, 1982. "Wound Tissue Can Utilize a Polymeric Template to Synthesize a Functional Extension of Skin." *Science*. vol. 215, No. 4529, pp. 174-176.

Montesano, R., L. Orci, and P. Vassalli. Nov. 1983. "In Vitro Rapid Organization of Endothelial Cells into Capillary-like Networks Is Promoted by Collagen Matrices." *The Journal of Cell Biology*. vol. 97, pp. 1648-1652.

Pierschbacher, Michael D. and Erkki Ruoslahti. May 3, 1984. "Cell Attachment Activity of Fibronectin Can Be Duplicated by Small Synthetic Fragments of the Molecule." *Nature*. vol. 309, pp. 30-33.

Landis, W. J. and J. R. Martin. Apr.-Jun. 1984. "X-Ray Photoelectron Spectroscopy Applied to Gold-Decorated Mineral Standards of Biological Interest" *J. Vac. Sci. Technol*. vol. A 2, No. 2, pp. 1108-1111.

Thompson, Nancy L., Adrienne A. Brian, and Harden M. McConnell. 1984. "Covalent Linkage of a Synthetic Peptide to a Fluorescent Phospholipid and Its Incorporation into Supported Phospholipid Monolayers." *Biochimica et Biophysica Acta*. vol. 772, pp. 10-19.

Yamada, Kimiho, Hirotaka Ihara, Toshio Ide, Takanori Fukumoto, and Chuichi Hirayama. 1984. "Formation of Helical Super Structure from Single-Walled Bilayers by Amphiphiles with Oligo-L-Glutamic Acid-Head Group." *Chemistry Letters*. No. 10, pp. 1713-1716.

Addadi, L. and S. Weiner. Jun. 15, 1985. "Interactions Between Acidic Proteins and Crystals: Stereochemical Requirements in Biomineralization." *Proceedings of the National Academy of Sciences of the United States of America*. vol. 82, No. 12, pp. 4110-4114.

"Public Health Service Policy on Humane Care and Use of Laboratory Animals." Sep. 1986. Office for Protection from Research Risks (OPRR), National Institutes of Health.

Weiner, Stephen and Wolfie Traub. Oct. 1986. "Organization of Hydroxyapatite Crystals Within Collagen Fibrils." *FEBS Letters*. vol. 206, No. 2, pp. 262-266.

Mann, Stephen, John P. Hannington, and R. J. P. Williams. Dec. 11, 1986. "Phospholipid Vesicles as a Model System for Biomineralization." *Nature*. vol. 324, pp. 565-567.

Krimm, Samuel and Jagdeesh Bandekar. 1986. "Vibrational Spectroscopy and Conformation of Peptides, Polypeptides, and Proteins." *Advances in Protein Chemistry*. vol. 38, pp. 181-364.

de Groot, K., R. Geesink, C. P. A. T. Klein, and P. Serekian. Dec. 1987. "Plasma Sprayed Coatings of Hydroxylapatite." *Journal of Biomedical Materials Research*. vol. 21, No. 12, pp. 1375-1381.

Bresnahan, J. C., M. S. Beattie, F. D. Todd III, and D. H. Noyes. 1987. "A Behavioral and Anatomical Analysis of Spinal Cord Injury Produced by a Feedback-Controlled Impaction Device." *Experimental Neurology*. vol. 95, pp. 548-570.

Moscatelli, David. 1987. "High and Low Affinity Binding Sites for Basic Fibroblast Growth Factor on Cultured Cells: Absence of a Role for Low Affinity Binding in the Stimulation of Plasminogen Activator Production by Bovine Endothelial Cells." *Journal of Cellular Physiology*, vol. 131, pp. 123-130.

Lambert, Joseph B., Herbert F. Shurvell, David A. Lightner, and R. Graham Cooks. 1987. "Group Frequencies: Infrared and Raman." *Introduction to Organic Spectroscopy*. New York: Macmillan Publishing Company. pp. 169-182.

Cook, Stephen D., Kevin A. Thomas, John F. Kay, and Michael Jarcho. Jul. 1988. "Hydroxyapatite-Coated Titanium for Orthopedic Implant Applications." *Clinical Orthopaedics and Related Research*. No. 232, pp. 225-243.

Saksela, Olli, David Moscatelli, Andreas Sommer, and Daniel B. Rifkin. Aug. 1988. "Endothelial Cell-Derived Heparan Sulfate Binds Basic Fibroblast Growth Factor and Protects It from Proteolytic Degradation." *The Journal of Cell Biology*. vol. 107, pp. 743-751.

Cardin, Alan D. and H. J. R. Weintraub. Jan./Feb. 1989. "Molecular Modeling of Protein-Glycosaminoglycan Interactions." *Arteriosclerosis*. vol. 9, No. 1, pp. 21-32.

Oonishi, H., M. Yamamoto, H. Ishii-Tiara, E. Tsuji, S. Kuskitani, M. Aono, and Y. Ukon. Mar. 1989. "The Effect of Hydroxyapatite Coating on Bone Growth into Porous Titanium Alloy Implants." *The Journal of Bone and Joint Surgery*. vol. 71-B, No. 2, pp. 213-216.

Friedmann, Theodore. Jun. 16, 1989. "Progress Toward Human Gene Therapy." *Science*. vol. 244, No. 4910, pp. 1275-1281.

Traub, Wolfie, Tahmon Arad, and Stephen Weiner. Dec. 15, 1989. "Three-Dimensional Ordered Distribution of Crystals in Turkey Tendon Collagen Fibers." *Proceedings of the National Academy of Sciences of the United States of America*. vol. 86, No. 24, pp. 9822-9826.

Knorr, Reinhard, Arnold Trzeciak, Willi Bannwarth, and Dieter Gillessen. 1989. "New Coupling Reagents in Peptide Chemistry." *Tetrahedron Letters*. vol. 30, No. 15, pp. 1927-1930.

Sambrook, Joseph, Edward F. Fritsch, and Thomas Maniatis. 1989. "Genes Encoding Selectable Markers." *Molecular Cloning: A Laboratory Manual*. $2^{nd}$ ed. New York: Cold Spring Harbor Laboratory Press. pp. 16.9-16.15.

Veis, A. 1989. "Biochemical Studies of Vertebrate Tooth Mineralization." *Biomineralization*. S. Mann, J. Webb, and R. J. P. Williams, editors. Weinheim, Federal Republic of Germany: VCH Verlagsgesellschaft and New York: VCH Publishers. pp. 189-222.

Schnell, Lisa and Martin E. Schwab. Jan. 18, 1990. "Axonal Regeneration in the Rat Spinal Cord Produced by an Antibody Against Myelin-Associated Neurite Growth Inhibitors." *Nature*. vol. 343, pp. 269-272.

Ahn, Sang Tae and Thomas A. Mustoe. Jan. 1990. "Effects of Ischemia on Ulcer Wound Healing: A New Model in the Rabbit Ear." *Annals of Plastic Surgery*. vol. 24, No. 1, pp. 17-23.

Van de Pol, Frans C. M. Dec. 1990. "Thin-Film ZnO—Properties and Applications." *Ceramic Bulletin*. vol. 69, No. 12, pp. 1959-1965.

Addadi, L., A. Berman, J. Moradian-Oldak, and S. Weiner. Dec. 28, 1990. "Tuning of Crystal Nucleation and Growth by Proteins: Molecular Interactions at Solid-Liquid Interfaces in Biomineralization." *Croatica Chemica Acta*. vol. 63, No. 3, pp. 539-544.

Sukenik, Chaim N., Natarajan Balachander, Lloyd A. Culp, Kristine Lewandowska, and Katherine Merritt. 1990. "Modulation of Cell Adhesion by Modification of Titanium Surfaces with Covalently Attached Self-Assembled Monolayers." *Journal of Biomedical Materials Research*. vol. 24, pp. 1307-1323.

Fields, C. G., D. H. Lloyd, R. L. Macdonald, K. M. Otteson, and R. L. Noble. Mar./Apr. 1991. "HBTU Activation for Automated Fmoc Solid-Phase Peptide Synthesis." *Peptide Research*. vol. 4, No. 2, pp. 95-101.

Murata, Masayuki, Satoshi Kagiwada, Sho Takahashi, and Shun-ichi Ohnishi. Aug. 5, 1991. "Membrane Fusion Induced by Mutual Interaction of the Two Charge-Reversed Amphiphilic Peptides at Neutral pH." *The Journal of Biological Chemistry*. vol. 56, No. 22, pp. 14353-14358.

Harris, Robin, Editor. 1991. *Electron Microscopy in Biology: A Practical Approach*. New York: Oxford University Press.

Jackson, David Y., David S. King, Jean Chmielewski, Sunil Singh, and Peter G. Schultz. 1991. "General Approach to the Synthesis of Short α-Helical Peptides." *Journal of the American Chemical Society*. vol. 113, pp. 9391-9392.

Polverini, Peter J., Noel P. Bouck, and Farzan Rastinejad. 1991. "Assay and Purification of Naturally Occurring Inhibitor of Angiogenesis." *Methods in Enzymology*. vol. 198, pp. 440-450.

Weiner, Stephen and Wolfie Traub. Feb. 1992. "Bone Structure: From Angstroms to Microns." *The FASEB Journal*. vol. 6, pp. 879-885.

Addadi, Lia and Stephen Weiner. 1992. "Control and Design Principles in Biological Mineralization." *Angew. Chem. Int. Ed. Engl*. vol. 31, pp. 153-169.

Beresford, J. N., J. H. Bennett, C. Devlin, P. S. Leboy, and M. E. Owen. 1992. "Evidence for an Inverse Relationship Between the Differentiation of Adipocytic and Osteogenic Cells in Rat Marrow Stromal Cell Cultures." *Journal of Cell Science*. vol. 102, pp. 341-351.

Cook, Stephen D., Kevin A. Thomas, Jeanette E. Dalton, Todd K. Volkman, Thomas S. Whitecloud III, and John F. Kay. 1992. "Hydroxylapatite Coating of Porous Implants Improves Bone Ingrowth and Interface Attachment Strength." *Journal of Biomedical Materials Research*. vol. 26, pp. 989-1001.

Geahlen, Robert L., G. Marc Loudon, Lisa A. Paige, and David Lloyd. 1992. "A General Method for Preparation of Peptides Biotinylated at the Carboxy Terminus." *Analytical Biochemistry*. vol. 202, pp. 68-70.

Ghadiri, M. Reza, Christopher Soares, and Chong Choi. 1992. "Design of an Artificial Four-Helix Bundle Metalloprotein via a Novel Ruthenium(II)-Assisted Self-Assembly Process." *Journal of the American Chemical Society*. vol. 114, No. 10, pp. 4000-4002.

Kunitake, Toyoki. 1992. "Synthetic Bilayer Membranes: Molecular Design, Self-Organization, and Application." *Angew. Chem. Int. Ed. Engl*. vol. 31, pp. 709-726.

Stapp, Samuel I. and Glenn W. Ciegler. 1992. "Organoapatites: Materials for Artificial Bone. I. Synthesis and Microstructure." *Journal of Biomedical Materials Research*. vol. 26, pp. 164-183.

Surewicz, Witold K., Henry H. Mantsch, and Dennis Chapman. Jan. 19, 1993. "Determination of Protein Secondary Structure by Fourier Transform Infrared Spectroscopy: A Critical Assessment." *Biochemistry*. vol. 32, No. 2, pp. 389-394.

Zhang, Shuguang, Todd Holmes, Curtis Lockshin, and Alexander Rich. Apr. 15, 1993. "Spontaneous Assembly of a Self-Complementary Oligopeptide to Form a Stable Macroscopic Membrane." *Proceedings of the National Academy of Sciences of the United States of America*. Vol. 90, No. 8, pp. 3334-3338.

Langer, Robert and Joseph P. Vacanti. May 14, 1993. "Tissue Engineering." *Science*. vol. 260, No. 5110, pp. 920-926.

Mulligan, Richard C. May 14, 1993. "The Basic Science of Gene Therapy." *Science*. vol. 260, No. 5110, pp. 926-932.

Massas, R., S. Pitaru, and M. M. Weinreb. Jun. 1993. "The Effects of Titanium and Hydroxyapatite on Osteoblastic Expression and Proliferation in Rat Parietal Bone Cultures." *Journal of Dental Research*. vol. 72, No. 6, pp. 1005-1008.

Archibald, Douglas D. and Stephen Mann. Jul. 29, 1993. "Template Mineralization of Self-Assembled Anisotropic Lipid Microstructures." *Nature*. vol. 364, pp. 430-433.

Atala, Anthony, Linda G. Cima, Wooseob Kim, Keith T. Paige, Joseph P. Vacanti, Alan B. Retik, and Charles A. Vacanti. Aug. 1993. "Injectable Alginate Seeded with Chondrocytes as a Potential Treatment for Vesicoureteral Reflux." *The Journal of Urology*. vol. 150, No. 2, pp. 745-747.

Ross-Murphy, S. B. and K. P. Shatwell. May-Aug. 1943. "Polysaccharide Strong and Weak Gels." *Biorheology*. vol. 30, Nos. 3 & 4, pp. 217-227.

Margalit, Hanah, Nurit Fischer, and Shmuel A. Ben-Sasson. Sep. 15, 1993. "Comparative Analysis of Structurally Defined Heparin Binding Sequences Reveals a Distinct Spatial Distribution of Basic Residues." *The Journal of Biological Chemistry*. vol. 268, No. 26, pp. 19228-19231.

Fowler, Bruce O., Milenko Marković, and Walter E. Brown. 1993. "Octacalcium Phosphate. 3. Infrared and Raman Vibrational Spectra." *Chem. Mater*. vol. 5 No. 10, pp. 1417-1423.

Fuhrhop, Jürgen-Hinrich, Dragan Spiroski, and Christoph Boettcher. 1993. "Molecular Monolayer Rods and Tubules Made of α-(L-Lysine),ω-(Amino) Bolaamphiphiles." *Journal of the American Chemical Society*. vol. 115, No. 4, pp. 1600-1601.

Graham, Stephan and Paul W. Brown. 1993. "The Low Temperature Formation of Octacalcium Phosphate." *Journal of Crystal Growth*. vol. 132, pp. 215-225.

Shimizu, Toshimi and Masakatsu Hato. 1993. "Self-Assembling Properties of Synthetic Peptidic Lipids." *Biochimica et Biophysica Acta*. vol. 1147, pp. 50-58.

Stupp, Samuel I., Jacqueline A. Hanson, Jo Ann Eurell, Glenn W. Ciegler, and Ann Johnson. 1993. "Organoapatites: Materials for Artifical Bone. III. Biological Testing." *Journal of Biomedical Materials Research*. vol. 27, pp. 301-311.

Stupp, Samuel I., George C. Mejicano, and Jacqueline A. Hanson. 1993. "Organoapatites: Materials for Artificial Bone. II. Hardening Reactions and Properties." *Journal of Biomedical Materials Research*. vol. 27, pp. 289-299.

Wald, Heidi L., Georgios Sarakinos, Michelle D. Lyman, Antonios G. Mikos, Joseph P. Vacanti, and Robert Langer. 1993. "Cell Seeding in Porous Transplantation Devices." *Biomaterials*. vol. 14, No. 4, pp. 270-278.

Walsh, Dominic, Joanne L. Kingston, Brigid R. Heywood, and Stephen Mann. 1993. "Influence of Monosaccharides and Related Molecules on the Morphology of Hydroxyapatite." *Journal of Crystal Growth*. vol. 133, pp. 1-12.

Wang, B. C., T. M. Lee, E. Chang, and C. Y. Yang. 1993. "The Shear Strength and the Failure Mode of Plasma-Sprayed Hydroxyapatite Coating to Bone: The Effect of Coating Thickness." *Journal of Biomedical Materials Research*. vol. 27, pp. 1315-1327.

San Antonio, James D., Arthur D. Lander, Morris J. Karnovsky, and Henry S. Slayter. Jun. 1994. "Mapping the Heparin-Binding Sites on Type I Collagen Monomers and Fibrils." *The Journal of Cell Biology*. vol. 125, No. 5, pp. 1179-1188.

Ban, S., S. Maruno, H. Iwata, and H. Itoh. 1994. "Calcium Phosphate Precipitation on the Surface of HA-G-Ti Composite Under Physiologic Conditions." *Journal of Biomedical Materials Research*. vol. 28, pp. 65-71.

de Bruijn, J. D., Y. P. Bovell, and C. A. van Blitterswijk. 1994. "Structural Arrangements at the Interface Between Plasma Sprayed Calcium Phosphates and Bone." *Biomaterials*. vol. 15, No. 7, pp. 543-550.

Hunter, Graeme K. and Harvey A. Goldberg. 1994. "Modulation of Crystal Formation by Bone Phosphoproteins: Role of Glutamic Acid-Rich Sequences in the Nucleation of Hydroxyapatite by Bone Sialoprotein." *Biochem. J.* vol. 302, pp. 175-179.

Klein, C. P. A. T., J. G. C. Wolke, J. M. A. de Blieck-Hogervorst, and K. de Groot. 1994. "Calcium Phosphate Plasma-Sprayed Coatings and Their Stability: An in Vivo Study." *Journal of Biomedical Materials Research*. vol. 28, pp. 909-917.

Mikos, Antonios G., Michelle D. Lyman, Lisa E. Freed, and Robert Langer. 1994. "Wetting of Poly(L-Lactic Acid) and Poly(DL-Lactic-co-glycolic Acid) Foams for Tissue Culture." *Biomaterials*. vol. 15, No. 1, pp. 55-58.

Bond, G. M., R. H. Richman, and W. P. McNaughton. Jun. 1995. "Mimicry of Natural Material Designs and Processes." *Journal of Materials Engineering and Performance*. vol. 4, No. 3, pp. 334-345.

Hubbell, Jeffrey A. Jun. 1995. "Biomaterials in Tissue Engineering." *Bio/technology*. vol. 13, pp. 565-576.

Fromm, J. R., R. E. Hileman, E. E. O. Caldwell, J. M. Weiler, and R. J. Linhardt. Nov. 10, 1995. "Differences in the Interaction of Heparin with Arginine and Lysine and the Importance of these Basic Amino Acids in the Binding of Heparin to Acidic Fibroblast Growth Factor." *Archives of Biochemistry and Biophysics*. vol. 323, No. 2, pp. 279-287.

Wakitani, Shigeyuki, Tomoyuki Saito, and Arnold I. Caplan. Dec. 1995. "Myogenic Cells Derived from Rat Bone Marrow Mesenchymal Stem Cells Exposed to 5-Azacytidine." *Muscle & Nerve*. vol. 18, pp. 1417-1426.

Aletras, Alexios, Kleomenis Barlos, Dimitrios Gatos, Sophia Koutsogianni, and Petros Mamos. 1995. "Preparation of the Very Acid-Sensitive Fmoc-Lys(Mtt)-OH." *International Journal of Peptide & Protein Research*. vol. 45, pp. 488-496.

Berndt, Peter, Gregg B. Fields, and Matthew Tirrell. 1995. "Synthetic Lipidation of Peptides and Amino Acids: Monolayer Structure and Properties." *Journal of the American Chemical Society*. vol. 117, No. 37, pp. 9515-9522.

Gage, Fred H., Jasodhara Ray, and Lisa J. Fisher. 1995. "Isolation, Characterization, and Use of Stem Cells from the CNS." *Annual Review of Neuroscience*. vol. 18, pp. 159-192.

Nomizu, Motoyoshi, Benjamin S. Weeks, Christi A. Weston, Woo Hoo Kim, Hynda K. Kleinman, and Yoshihiko Yamada. 1995. "Structure-Activity Study of a Laminin α1 Chain Active Peptide Segment Ile-Lys-Val-Ala-Val (IKVAV)." *FEBS Letters*. vol. 365, pp. 227-231.

Saito, Tomoyuki, James E. Dennis, Donald P. Lennon, Randell G. Young, and Arnold I. Caplan. 1995. "Myogenic Expression of Mesenchymal Stem Cells Within Myotubes of *mdx* Mice in Vitro and in Vivo." *Tissue Engineering*. vol. 1, No. 4, pp. 327-343.

Sasanuma, Michio. 1995. "Optical Processes in ZnO." *J. Phys.: Condens. Matter*. vol. 7, pp. 10029-10036.

Zhang, Shuguang, Todd C. Holmes, C. Michael DiPersio, Richard O. Hynes, Xing Su, and Alexander Rich. 1995. "Self-Complementary Oligopeptide Matrices Support Mammalian Cell Attachment." *Biomaterials*. vol. 16, No. 18, pp. 1385-1393.

Falini, Guiseppe, Shira Albeck, Steve Weiner, and Lia Addadi. Jan. 5, 1996. "Control of Aragonite or Calcite Polymorphism by Mollusk Shell Macromolecules." *Science*. vol. 271, No. 5245, pp. 67-69.

Alivisatos, A. P. Feb. 16, 1996. "Semiconductor Clusters, Nanocrystals, and Quantum Dots." *Science*. vol. 271, No. 5251, pp. 933-937.

Keyt, Bruce A., Lea T. Berleau, Hung V. Nguyen, Helen Chen, Henry Heinsohn, Richard Vandlen, and Napoleone Ferrara. Mar. 29, 1996. "The Carboxyl-terminal Domain (111-165) of Vascular Endothelial Growth Factor Is Critical for Its Mitogenic Potency." *The Journal of Biological Chemistry*. vol. 271, No. 13, pp. 7788-7795.

Belcher, A. M., X. H. Wu, R. J. Christensen, P. K. Hansma, G. D. Stucky, and D. E. Morse. May 2, 1996. "Control of Crystal Phase Switching and Orientation by Soluble Mullusc-Shell Proteins." *Nature*. vol. 381, pp. 56-58.

Hortelano, Gonzalo, Ayman Al-Hendy, Frederick A. Ofosu, and Patricia L. Chang. Jun. 15, 1996. "Delivery of Human Factor IX in Mice by Encapsulated Recombinant Myoblasts: A Novel Approach Towards Allogenic Gene Therapy of Hemophilia B." *Blood*. vol. 87, No. 12, pp. 5095-5103.

Sultzbaugh, K. J. and T. J. Speaker. Jul.-Aug. 1996. "A Method to Attach Lectins to the Surface of Spermine Alginate Microcapsules Based on the Avidin Biotin Interaction." *J. Microencapsulation*. vol. 13, No. 4, pp. 363-375.

Alivisatos, A. Paul, Kai P. Johnsson, Xiaogang Peng, Troy E. Wilson, Colin J. Loweth, Marcel P. Burchez Jr., and Peter G. Schultz. Aug. 15, 1996. "Organization of 'Nanocrystal Molecules' Using DNA." *Nature*. vol. 382, pp. 609-611.

George, Anne, Leslie Bannon, Boris Sabsay, Jerry W. Dillon, James Malone, Arthur Veis, Nancy A. Jenkins, Debra J. Gilbert, and Neal G. Copeland. Dec. 20, 1996. "The Carboxyl-terminal Domain of Phosphophoryn Contains Unique Extended Triplet Amino Acid Repeat Sequences Forming Ordered Carboxyl-Phosphate Interaction Ridges That May Be Essential in the Biomineralization Process." *The Journal of Biological Chemistry*. vol. 271, No. 51, pp. 32869-32873.

Basso, D. Michele, Michael S. Beattie, and Jacqueline C. Bresnahan. 1996. "Graded Histological and Locomotor Outcomes after Spinal Cord Contusion Using the NYU Weight-Drop Device Versus Transection." *Experimental Neurology*. vol. 139, pp. 244-256.

Burkett, Sandra L. and Stephen Mann. 1996. "Spatial Organization and Patterning of Gold Nanoparticles on Self-Assembled Biolipid Tubular Templates." *Chem. Commun*. pp. 321-322.

Hunter, Graeme K., Peter V. Hauschka, A. Robin Poole, Lawrence C. Rosenberg, and Harvey A. Goldberg. 1996. "Nucleation and Inhibition of Hydroxyapatite by Mineralized Tissue Proteins." *Biochem. J.* vol. 317, pp. 59-64.

Karymov, Mikhail A., Karel Procházka, John M. Mendenhall, Thomas J. Martin, Petr Munk, and Stephen E. Webber. 1996. "Chemical Attachment of Polystyrene-*block*-poly(methacrylic acid) Micelles on a Silicon Nitride Surface." *Langmuir*. vol. 12, No. 20, 4748-4753.

Landis, William J., Karen J. Hodgens, James Arena, Min Ja Song, and Bruce F. McEwen. 1996. "Structural Relations Between Collagen and Mineral in Bone as Determined by High Voltage Electron Microscopic Tomography." *Microscopy Research and Technique*. vol. 33, pp. 192-202.

Matsuzawa, Mieko, Forrest F. Weight, Richard S. Potember, and Päivi Liesi. 1996. "Directional Neurite Outgrowth and Axonal Differentiation of Embryonic Hippocampal Neurons Are Promoted by a Neurite Outgrowth Domain of the B2-Chain of Laminin." *Int. J. Devl. Neuroscience*. vol. 14, No. 3, pp. 283-295.

Mooney, David J., Daniel F. Baldwin, Nam P. Suh, Joseph P. Vacanti, and Robert Langer. 1996. "Novel Approach to Fabricate Porous Sponges of Poly(D,L-Lactic-co-glycolic Acid) Without the Use of Organic Solvents." *Biomaterials*. vol. 17, No. 14, pp. 1417-1422.

Ratner, Buddy D., Allan S. Hoffman, Frederick J. Schoen, and Jack E. Lemons, Editors. 1996. *Biomaterials Science: An Introduction to Materials in Medicine*. San Diego, CA: Academic Press.

Ulman, Abraham. 1996. "Formation and Structure of Self-Assembled Monolayers." *Chemical Reviews*. vol. 96, No. 4, pp. 1533-1554.

Yu, Ying-Ching, Peter Berndt, Matthew Tirrell, and Gregg B. Fields. 1996. "Self-Assembling Amphiphiles for Construction of Protein Molecular Architecture." *Journal of the American Chemical Society*. vol. 118, No. 50, pp. 12515-12520.

Zarif, Leila, Ange Polidori, Bernard Pucci, Tadek Gulik-Krzywicki, André A. Pavia, and Jean G. Riess. 1996. "Effect of Chirality on the Formation of Tubules from Glycolipidic Amphiphiles." *Chemistry and Physics of Lipids*. vol. 79, pp. 165-170.

Aggeli, A., M. Bell, N. Boden, J. N. Keen, P. F. Knowles, T. C. B. McLeish, M. Pitkeathly, and S. E. Radford. Mar. 20, 1997. "Responsive Gels Formed by the Spontaneous Self-Assembly of Peptides into Polymeric β-Sheet Tapes." *Nature*. vol. 386, pp. 259-262.

Herr, Andrew B., David M. Ornitz, Ram Sasisekharan, Ganesh Venkataraman, and Gabriel Waksman. Jun. 27, 1997. "Heparin-Induced Self-Association of Fibroblast Growth Factor-2." *The Journal of Biological Chemistry*. vol. 272, No. 26, pp. 16382-16389.

Dimmeler, Stefanie and Andreas M. Zeiher. Aug. 1997. "Nitric Oxide and Apoptosis: Another Paradigm for the Double-Edged Role of Nitric Oxide." *Nitric Oxide: Biology and Chemistry*. vol. 1, No. 4, pp. 275-281.

Stupp, Samuel I. and Paul V. Braun. Aug. 29, 1997. "Molecular Manipulation of Microstructures: Biomaterials, Ceramics, and Semiconductors." *Science*. vol. 277, No. 5330, pp. 1242-1248.

Kaufmann, P. M., S. Heimrath, B. S. Kim, and D. J. Mooney. Sep./Oct. 1997. "Highly Porous Polymer Matrices as a Three-Dimensional Culture System for Hepatocytes." *Cell Transplantation*. vol. 6, No. 5, pp. 463-468.

Aggeli, Amalia, Mark Bell, Neville Boden, Jeff N. Keen, Tom C. B. McLeish, Irina Nyrkova, Sheena E. Radford, and Alexander Semenov. 1997. "Engineering of Peptide β-Sheet Nanotapes." *J. Mater. Chem*. vol. 7, No. 7, pp. 1135-1145.

Anderson, James M. and Matthew S. Shive. 1997. "Biodegradation and Biocompatibility of PLA and PLGA Microspheres." *Advanced Drug Delivery Reviews*. vol. 28, pp. 5-24.

Draget, Kurt Ingar, Gudinund Skjåk-Bræ, Olav Smidsrød. 1997. "Alginate Based New Materials." *International Journal of Biological Macromolecules*. vol. 21, pp. 47-55.

El-Ghannam, Ahmed, Paul Ducheyne, and Irving M. Shapiro. 1997. "Porous Bioactive Glass and Hydroxyapatite Ceramic Affect Bone Cell Function In Vitro Along Different Time Lines." *Journal of Biomedical Materials Research*. vol. 36, pp. 167-180.

Jaiswal, Neelam, Stephen E. Haynesworth, Arnold I. Caplan, and Scott P. Bruder. 1997. "Osteogenic Differentiation of Purified, Culture-Expanded Human Mesenchymal Stem Cells In Vitro." *Journal of Cellular Biochemistry*, vol. 64, pp. 295-312.

Nehrer, Stefan, Howard A. Breinan, Arun Ramappa, Sonya Shortkroff, Gretchen Young, Tom Minas, Clement B. Sledge, Ioannis V. Yannas, and Myron Spector. 1997. "Canine Chondrocytes Seeded in Type I and Type II Collagen Implants Investigated In Vitro." *Journal of Biomedical Materials Research (Appl. Biomater.)*. vol. 38, pp. 95-104.

Mann, Stephen. 1997. "Biomineralization: The Form(id)able Part of Bioinorganic Chemistry!" *J. Chem. Soc., Dalton Trans*. pp. 3953-3961.

Norrby, Klas. 1997. "Angiogenesis: New Aspects Relating to Its Initiation and Control." *APMIS*. vol. 105, pp. 417-437.

Shimizu, Toshimi, Masaki Kogiso, and Mitsutoshi Masuda. 1997. "Noncovalent Formation of Polyglycine II-Type Structure by Hexagonal Self-Assembly of Linear Polymolecular Chains." *Journal of the Americal Chemical Society*. vol. 119, No. 26, pp. 6209-6210, S2-S17.

Smith, George P. and Valery A. Petrenko. 1997. "Phage Display." *Chemical Reviews*. vol. 97, No. 2, pp. 391-410.

Toyotama, Akiko, Shin-ichi Kugimiya, Masakatsu Yonese, Takatoshi Kinoshita, and Yoshiliani Tsujita. 1997. "Controllable Orientation of the Peptide-Based Surfactant at Air-Water Interface." *Chemistry Letters*. pp. 443-444.

Weiner, Stephen and Lia Addadi. 1997. "Design Strategies in Mineralized Biological Materials." *J. Mater. Chem*. vol. 7, No. 5, pp. 689-702.

Wellings, Donald A. and Eric Atherton. 1997. "Standard Fmoc Protocols." *Methods in Enzymology*. vol. 289, pp. 44-67.

Wen, H. B., J. G. C. Wolke, J. R. de Wijn, Q. Liu, F. Z. Cui, and K. de Groot. 1997. "Fast Precipitation of Calcium Phosphate Layers on Titanium Induced by Simple Chemical Treatments." *Biomaterials*. vol. 18, No. 22, pp. 1471-1478.

Yu, Ying-Ching, Teika Pakalns, Yoav Dori, James B. McCarthy, Matthew Tirrell, and Gregg B. Fields. 1997. "Construction of Biologically Active Protein Molecular Architecture Using Self-Assembling Peptide-Amphiphiles." *Methods in Enzymology*. vol. 289, pp. 571-587.

Zhitomirsky, I. and L. Gal-Or. 1997. "Electrophoretic Deposition of Hydroxyapatite." *Journal of Materials Science: Materials in Medicine*. pp. 213-219.

Veis, Arthur, Kuiru Wei, Charles Sfeir, Anne George, and James Malone. Jan. 1998. "Properties of the $(DSS)_n$ Triplet Repeat Domain of Rat Dentin Phosphophoryn." *European Journal of Oral Sciences*. vol. 106 (suppl. 1), pp. 234-238.

Pincus, David W., Robert R. Goodman, Richard A. R. Fraser, Maiken Nedergaard, and Steven A. Goldman. Apr. 1998. "Neural Stem and Progenitor Cells: A Strategy for Gene Therapy and Brain Repair." *Neurosurgery*. vol. 42, No. 4, pp. 858-867.

Ogiso, M., Y. Yamashita, and T. Matsumoto. Jun. 1998. "The Process of Physical Weakening and Dissolution of the HA-Coated Implant in Bone and Soft Tissue." *Journal of Dental Research*. vol. 77, No. 6, pp. 1426-1434.

Petka, Wendy A., James L. Harden, Kevin P. McGrath, Denis Wirtz, and David A. Tirrell. Jul. 17, 1998. "Reversible Hydrogels from Self-Assembling Artificial Proteins." *Science*. vol. 281, No. 5375, pp. 389-392.

Orgill, Dennis P., Charles Butler, John F. Regan, Mark S. Barlow, I. V. Yannas, and Carolyn C. Compton. Aug. 1998. "Vascularized Collagen-Glycosaminoglycan Matrix Provides a Dermal Substrate and Improves Take of Cultured Epithelial Autografts." *Plastic and Reconstructive Surgery*. vol. 102, No. 2, pp. 423-429.

Yu, Ying-Ching, Matthew Tirrell, and Gregg B. Fields. Oct. 7, 1998. "Minimal Lipidation Stabilizes Protein-Like Molecular Architecture." *Journal of the American Chemical Society*. vol. 120, No. 39, pp. 9979-9987.

Borkenhagen, M., J.-F. Clémence, H. Sigrist, and P. Aebischer. 1998. "Three-Dimensional Extracellular Matrix Engineering in the Nervous System." *Journal of Biomedical Materials Research*. vol. 40, pp. 392-400.

Brekke, John H. and Jeffrey M. Toth. 1998. "Principles of Tissue Engineering Applied to Programmable Osteogenesis." *Journal of Biomedical Materials Research (Appl. Biomater.)*. vol. 43, pp. 380-398.

Fields, Gregg B., Janelle L. Lauer, Yoav Dori, Pilar Forns, Ying-Ching Yu, and Matthew Tirrell. 1998. "Proteinlike Molecular Architecture: Biomaterial Applications for Inducing Cellular Receptor Binding and Signal Transduction." *Biopolymers (Peptide Science)*. vol. 47, pp. 143-151.

Gu, Keni, Syweren R. Chang, Matt S. Slaven, Brian H. Clarkson, R. Bruce Rutherford, and Helena H. Ritchie. 1998. "Human Dentin Phosphophoryn Nucleotide and Amino Acid Sequence." *European Journal of Oral Sciences*. vol. 106, pp. 1043-1047.

Hartgerink, Jeffrey D., Thomas D. Clark, and M. Reza Ghadiri. 1998. "Peptide Nanotubes and Beyond." *Chem. Eur. J*. vol. 4, No. 8, pp. 1367-1372.

Johnstone, Brian, Thomas M. Hering, Arnold I. Caplan, Victor M. Goldberg, and Jung U. Yoo. 1998. "In Vitro Chondrogenesis of Bone Marrow-Derived Mesenchymal Progenitor Cells." *Experimental Cell Research*. vol. 238, pp. 265-272.

Kawasaki, M., A. Ohtomo, I. Ohkubo, H. Koinuma, Z. K. Tang, P. Yu, G. K. L. Wong, B. P. Zhang, and Y. Segawa. 1998. "Excitonic Ultraviolet Laser Emission at Room Temperature from Naturally Made Cavity in ZnO Nanocrytal Thin Films." *Materials Science and Engineering*. vol. B56, pp. 239-245.

Kogiso, Masaki, Satomi Ohnishi, Kiyoshi Yase, Mitsutoshi Masuda, and Toshimi Shimizu. 1998. "Dicarboxylic Oligopeptide Bolaamphiphiles: Proton-Triggered Self-Assembly of Microtubes with Loose Solid Surfaces." *Langmuir*. vol. 14, No. 18, pp. 4978-4986, S1-S7.

Kogiso, Masaki, Takeshi Hanada, Kiyoshi Yase, and Toshimi Shimizu. 1998. "Intralayer Hydrogen-Bond-Directed Self-Assembly of Nano-Fibers from Dicarboxylic Valylvaline Bolaamphiphiles." *Chem. Comm.* pp. 1791-1792.

Li, Panjian and Paul Ducheyne. 1998. "Quasi-Biological Apatite Film Induced by Titanium in a Simulated Body Fluid." *Journal of Biomedical Materials Research.* vol. 41, pp. 341-348.

Nanci, A., J. D. Wuest, L. Peru, P. Brunet, V. Sharma, S. Zalzal, and M. D. McKee. 1998. "Chemical Modification of Titanium Surfaces for Covalent Attachment of Biological Molecules." *Journal of Biomedical Materials Research.* vol. 40, pp. 324-335.

Tsui, Y. C., C. Doyle, and T. W. Clyne. 1998. "Plasma Sprayed Hydroxyapatite Coatings on Titanium Substrates Part 2: Optimisation of Coating Properties." *Biomaterials.* vol. 19, pp. 2031-2043.

Weiner, S. and H. D. Wagner. 1998. "The Material Bone: Structure-Mechanical Function Relations." *Annu. Rev. Mater. Sci.* vol. 28, pp. 271-298.

Wen, H. B., J. R. de Wijn, F. Z. Cui, and K. de Groot. 1998. "Preparation of Calcium Phosphate Coatings on Titanium Implant Materials by Simple Chemistry." *Journal of Biomedical Materials Research.* vol. 41, pp. 227-236.

Wheeler, Donna L., David L. Chamberland, John M. Schmitt, David C. Buck, John H. Brekke, Jeffrey O. Hollinger, S.-P. Joh, and K.-W. Suh. 1998. "Radiomorphometry and Biomechanical Assessment of Recombinant Human Bone Morphogenetic Protein 2 and Polymer in Rabbit Radius Ostectomy Model." *Journal of Biomedical Materials Research (Appl. Biomater.).* vol. 43, pp. 365-373.

Wolke, J. G. C., K. de Groot, and J. A. Jansen. 1998. "In Vivo Dissolution Behavior of Various RF Magnetron Sputtered Ca-P Coatings." *Journal of Biomedical Materials Research.* vol. 39, pp. 524-530.

Xiao, Shou-Jun, Marcus Textor, and Nicholas D. Spencer. 1998. "Covalent Attachment of Cell-Adhesive, (Arg-Gly-Asp)-Containing Peptides to Titanium Surfaces." *Langmuir.* vol. 14, No. 19, pp. 5507-5516.

Xu, Guofeng, Nan Yao, Ilhan A. Aksay, and John T. Groves. 1998. "Biomimetic Synthesis of Macroscopic-Scale Calcium Carbonate Thin Films. Evidence for a Multistep Assembly Process." *Journal of the American Chemical Society.* vol. 120, No. 46, pp. 11977-11985.

Yamada, Norihiro, Katsuhiko Ariga, Masanobu Naito, Kazuhiro Matsubara, and Emiko Koyama. 1998. "Regulation of β-Sheet Structures Within Amyloid-Like β-Sheet Assemblage from Tripeptide Derivatives." *Journal of the American Chemical Society.* vol. 120, No. 47, pp. 12192-12199.

Chusuei, Charles C., D. Wayne Goodman, Michael J. Van Stipdonk, Dina R. Justes, and Emile A. Schweikert. Jan. 1, 1999. "Calcium Phosphate Phase Identification Using XPS and Time-of-Flight Cluster SIMS." *Analytical Chemistry.* vol. 71, No. 1, pp. 149-153.

Zubarev, Eugene R., Martin U. Pralle, Leiming Li, and Samuel I. Stupp. Jan. 22, 1999. "Conversion of Supramolecular Clusters to Macromolecular Objects." *Science.* vol. 283, pp. 523-526.

Won, You-Yeon, H. Ted Davis, and Frank S. Bates. Feb. 12, 1999. "Giant Wormlike Rubber Micelles." *Science.* vol. 283, No. 5404, pp. 960-963.

Corral, Claudio J., Aamir Siddiqui, Liancun Wu, Catherine L. Farrell, David Lyons, and Thomas A. Mustoe. Feb. 1999. "Vascular Endothelial Growth Factor Is More Important Than Basic Fibroblastic Growth Factor During Ischemic Wound Healing." *Arch. Surg.* vol. 134, pp. 200-205.

Wheeler, B. C., J. M. Corey, G. J. Brewer, and D. W. Branch. Feb. 1999. "Microcontact Printing for Precise Control of Nerve Cell Growth in Culture." *Journal of Biomechanical Engineering.* vol. 121, pp. 73-78.

Cao, H., Y. G. Zhao, S. T. Ho, E. W. Seelig, Q. H. Wang, and R. P. H. Chang. Mar. 15, 1999. "Random Laser Action in Semiconductor Powder." *Physical Review Letters.* vol. 82, No. 11, pp. 2278-2281.

Aizenberg, Joanna, Andrew J. Black, and George M. Whitesides. Apr. 8, 1999. "Control of Crystal Nucleation by Patterned Self-Assembled Monolayers." *Nature.* vol. 398, pp. 495-498.

Niklason, L. E., J. Gao, W. M. Abbott, K. K. Hirschi, S. Houser, R. Marini, and R. Langer. Apr. 16, 1999. "Functional Arteries Grown in Vitro." *Science.* vol. 284, pp. 489-493.

Hahn, Jungseok and Stephen E. Webber. Apr. 1999. "Modification of Surfaces by Covalent Attachment of Polymer Micelles." *Macromolecular Symposia.* vol. 139, pp. 39-47.

Liu, Yi, Duckhyun Kim, B. Timothy Himes, Stella Y. Chow, Timothy Schallert, Marion Murray, Alan Tessler, and Itzhak Fischer. Jun. 1, 1999. "Transplants of Fibroblasts Genetically Modified to Express BDNF Promote Regeneration of Adult Rat Rubrospinal Axons and Recovery of Forelimb Function." *The Journal of Neuroscience.* vol. 19, No. 11, pp. 4370-4387.

Mehler, Mark F. and John A. Kessler. Jul. 1999. "Progenitor Cell Biology: Implications for Neural Regeneration." *Arch. Neurol.* vol. 56, pp. 780-784.

Tirrell, M. Oct. 27, 1999. "Biofunctionalization of Surfaces with Peptide Amphiphiles." *AVS: Science & Technology.* Invited Paper BI-WeM7.

McDonald, John W., Xiao-Zhong Liu, Yun Qu, Su Liu, Shannon K. Mickey, Dorothy Turetsky, David I. Gottlieb, and Dennis W. Choi. Dec. 1999. "Transplanted Embryonic Stem Cells Survive, Differentiate and Promote Recovery in Injured Rat Spinal Cord." *Nature Medicine.* vol. 5, No. 12, pp. 1410-1412.

Bradt, Jens-Hilmar, Michael Mertig, Angelika Teresiak, and Wolfgang Pompe. 1999. "Biomimetic Mineralization of Collagen by Combined Fibril Assembly and Calcium Phosphate Formation." *Chem. Mater.* vol. 11, No. 10, pp. 2694-2701.

Braun, Paul V. and Samuel I. Stupp. 1999. "CdS Mineralization of Hexagonal, Lamellar, and Cubic Lyotropic Liquid Crystals." *Materials Research Bulletin.* vol. 34, No. 3, pp. 463-469.

Butler, C. E., I. V. Yannas, C. C. Compton, C. A. Correia, and D. P. Orgill. 1999. "Comparison of Cultured and Uncultured Keratinocytes Seeded into a Collagen-GAG Matrix for Skin Replacements." *British Journal of Plastic Surgery.* vol. 52, pp. 127-132.

Chai, C. S. and B. Ben-Nissan. 1999. "Bioactive Nanocrystalline Sol-Gel Hydroxyapatite Coatings." *Journal of Materials Science: Materials in Medicine.* vol. 10, pp. 465-469.

Clark, Thomas D., Kenji Kobayashi, and M. Reza Ghadiri. 1999. "Covalent Capture and Stabilization of Cylindrical β-Sheet Peptide Assemblies." *Chem. Eur. J.* vol. 5, No. 2, pp. 782-792.

Cornish, J., K. E. Callon, C. Q.-X. Lin, C. L. Xiao, T. B. Mulvey, G. J. S. Cooper, and I. R. Reid. 1999. "Trifluoroacetate, a Contaminant in Purified Proteins, Inhibits Proliferation of Osteoblasts and Chondrocytes." *Am. J. Physio!. Endocrinol. Metab.* vol. 277, pp. 779-783.

Emoto, Kazunori, Yukio Nagasaki, and Kazunori Kataoka. 1999. "Coating of Surfaces with Stabilized Reactive Micelles from Poly-(ethylene glycol)—Poly(DL-Lactic Acid) Block Copolymer." *Langmuir.* vol. 15, No. 16, pp. 5212-5218.

Fields, Gregg B. 1999. "Induction of Protein-like Molecular Architecture by Self-Assembly Processes." *Bioorganic & Medicinal Chemistry.* vol. 7, pp. 75-81.

Haynes, Andrew J., Wei-Qun Huang, Jamie Mallah, Dajun Yang, Marc E. Lippman, and Lu-Yuan Li. 1999. "Angiopoietin-1 and Its Receptor Tie-2 Participate in the Regulation of Capillary-like Tubule Formation and Survival of Endothelial Cells." *Microvascular Research.* vol. 58, pp. 224-237.

Hwang, Julia J., Kevin Jaeger, James Hancock, and Samuel I. Stupp. 1999. "Organoapatite Growth on an Orthopedic Alloy Surface." *Journal of Biomedical Materials Research.* vol. 47, pp. 504-515.

Ignjatović, Nenad, Simonida Tomić, Momčilo Dakić, Miroslav Miljković, Milenko Plavšić, and Dragan Uskoković. 1999. "Synthesis and Properties of Hydroxyapatite/Poly-L-Lactide Composite Biomaterials." *Biomaterials.* vol. 20, pp. 809-816.

Lee, Kevin J. and Thomas M. Jessell. 1999. "The Specification of Dorsal Cell Fates in the Vertebrate Central Nervous System." *Annual Review of Neuroscience.* vol. 22, pp. 261-294.

Lee, Kyujin C., Paul A. Carlson, Alex S. Goldstein, Paul Yager, and Michael H. Gelb. 1999. "Protection of a Decapeptide from Proteolytic Cleavage by Lipidation and Self-Assembly into High-Axial-Ratio Microstructures: A Kinetic and Structural Study." *Langmuir.* vol. 15, No. 17, pp. 5500-5508.

Mao, Chuanbin, Hengde Li, Fuzhai Cui, Chunlai Ma, and Qinglin Feng. 1999. "Oriented Growth of Phosphates on Polycrystalline Titanium in a Process Mimicking Biomineralization." *Journal of Crystal Growth.* vol. 206, pp. 308-321.

Miyaji, Fumiaki, Hyun-Min Kim, Shinichi Handa, Tadashi Kokubo, and Takashi Nakamura. 1999. "Bonelike Apatite Coating on Organic Polymers: Novel Nucleation Process Using Sodium Silicate Solution." *Biomaterials*. vol. 20, pp. 913-919.

Pakalns, Teika, Kraig L. Haverstick, Gregg B. Fields, James B. McCarthy, Daniel L. Mooradian, and Matthew Tirrell. 1999. "Cellular Recognition of Synthetic Peptide Amphiphiles in Self-Assembled Monolayer Films." *Biomaterials*. vol. 20, pp. 2265-2279.

Pittenger, Mark F., Alastair M. Mackay, Stephen C. Beck, Rama K. Jaiswal, Robin Douglas, Joseph D. Mosca, Mark A. Moorman, Donald W. Simonetti, Stewart Craig, and Daniel R. Marshak. Apr. 2, 1999. "Multilineage Potential of Adult Human Mesenchymal Stem Cells." *Science*. vol. 284, pp. 143-147.

Rezania, Alireza, Robert Johnson, Anthony R. Lefkow, and Kevin E. Healy. 1999. "Bioactivation of Metal Oxide Surfaces. 1. Surface Characterization and Cell Response." *Langmuir*. vol. 15, No. 20, pp. 6931-6939.

Rowley, Jon A., Gerard Madlambayan, and David J. Mooney. 1999. "Alginate Hydrogels as Synthetic Extracellular Matrix Materials." *Biomaterials*. vol. 20, pp. 45-53.

Schense, Jason C. and Jeffrey A. Hubbell. 1999. "Cross-Linking Exogenous Bifunctional Peptides into Fibrin Gels with Factor XIIIa." *Bioconjugate Chem*. vol. 10, No. 1, pp. 75-81.

Varma, H. K., Y. Yokogawa, F. F. Espinosa, Y. Kawamoto, K. Nishizawa, F. Nagata, and T. Kameyama. 1999. "In-Vitro Calcium Phosphate Growth over Functionalized Cotton Fibers." *Journal of Materials Science: Materials in Medicine*. vol. 10, pp. 395-400.

Vernon, Robert B. and E. Helene Sage. 1999. "A Novel, Quantitative Model for Study of Endothelial Cell Migration and Sprout Formation Within Three-Dimensional Collagen Matrices." *Microvascular Research*. vol. 57, pp. 188-133.

Wei, M., A. J. Ruys, M. V. Swain, S. H. Kim, B. K. Milthorpe, and C. C. Sorrell. 1999. "Interfacial Bond Strength of Electrophoretically Deposited Hydroxyapatite Coatings on Metals." *Journal of Materials Science: Materials in Medicine*. vol. 10, pp. 401-409.

Yu, Ying-Ching, Vikram Roontga, Vladimir A. Daragan, Kevin H. Mayo, Matthew Tirrell, and Gregg B. Fields. 1999. "Structure and Dynamics of Peptide—Amphiphiles Incorporating Triple-Helical Proteinlike Molecular Architecture." *Biochemistry*. vol. 38, No. 5, pp. 1659-1668.

Huq, N. Laila, Keith J. Cross, and Eric C. Reynolds. Feb. 4, 2000. "Molecular Modelling of a Multiphosphorylated Sequence Motif Bound to Hydroxyapatite Surfaces." *Journal of Molecular Modeling*. vol. 6, pp. 35-47.

Martinez, J. S., G. P. Zhang, P. D. Holt, H.—T. Jung, C. J. Carrano, M. G. Haygood, and Alison Butler. Feb. 18, 2000. "Self-Assembling Amphiphilic Siderophores from Marine Bacteria." *Science*. vol. 287, No. 5456, pp. 1245-1247.

Verrecchio, Angela, Markus W. Germann, Barbara P. Schick, Brian Kung, Thomas Twardowski, and James D. San Antonio. Mar. 17, 2000. "Design of Peptides with High Affinities for Heparin and Endothelial Cell Proteoglycans." *The Journal of Biological Chemistry*. vol. 275, No. 11, pp. 7701-7707.

Cao, H., J. Y. Xu, E. W. Seelig, and R. P. H. Chang. May 22, 2000. "Microlaser Made of Disordered Media." *Applied Physics Letters*. vol. 76, No. 21, pp. 2997-2999.

Marler, Jennifer J., Amrita Guha, Jonathan Rowley, Rahul Koka, David Mooney, Joseph Upton, and Joseph Vacanti. May 2000. "Soft-Tissue Augmentation with Injectable Alginate and Syngeneic Fibroblasts." *Plastic and Reconstructive Surgery*. vol. 105, No. 6, pp. 2049-2058.

Holmes, Todd C., Sonsoles de Lacalle, Xing Su, Guosong Liu, Alexander Rich, and Shuguang Zhang. Jun. 6, 2000. "Extensive Neurite Outgrowth and Active Synapse Formation on Self-Assembling Peptide Scaffolds." *Proceedings of the National Academy of Sciences of the United States of America*. vol. 97, No. 12, pp. 6728-6733.

Whaley, Sandra R., D. S. English, Evelyn L. Hu, Paul F. Barbara, and Angela M. Belcher. Jun. 8, 2000. "Selection of Peptides with Semiconductor Binding Specificity for Directed Nanocrystal Assembly." *Nature*. vol. 405, pp. 665-668.

Sun, Xiu-xia and Chi-chen Wang. Jul. 28, 2000. "The N-Terminal Sequence (Residues 1-65) Is Essential for Dimerization, Activities, and Peptide Binding of *Escherichia coli* DsbC." *The Journal of Biological Chemistry*. vol. 275, No. 30, pp. 22743-22749.

Hsu, Wei-Cherng, Mark H. Spilker, Ioannis V. Yannas, and Peter A. D. Rubin. Aug. 2000. "Inhibition of Conjunctival Scarring and Contraction by a Porous Collagen-Glycosaminoglycan Implant." *Investigative Ophthalmology & Visual Science*. vol. 41, No. 9, pp. 2404-2411.

Schlessinger, Joseph, Alexander N. Plotnikov, Omar A. Ibrahimi, Anna V. Eliseenkova, Brian K. Yeh, Avner Yayon, Robert J. Linhardt, and Moosa Mohammadi. Sep. 2000. "Crystal Structure of a Ternary FGF-FGFR-Heparin Complex Reveals a Dual Role for Heparin in FGFR Binding and Dimerization." *Molecular Cell*. vol. 6, pp. 743-750.

Sun, Y., J. B. Ketterson, and G. K. L. Wong. Oct. 9, 2000. "Excitonic Gain and Stimulated Ultraviolet Emission in Nanocrystalline Zinc-Oxide Powder." *Applied Physics Letters*. vol. 77, No. 15, pp. 2322-2324.

Schuldiner, Maya, Ofra Yanuka, Joseph Itskovitz-Eldor, Douglas A. Melton, and Nissim Benvenisty. Oct. 10, 2000. "Effects of Eight Growth Factors on the Differentiation of Cells Derived from Human Embryonic Stem Cells." *Proceedings of the National Academy of Sciences of the United States of America*. vol. 97, No. 21, pp. 11307-11312.

Altman, Michael, Peter Lee, Alexander Rich, and Shuguang Zhang. 2000. "Conformational Behavior of Ionic Self-Complementary Peptides." *Protein Science*. vol. 9, pp. 1095-1105.

Archer, Eric A., Noah T. Goldberg, Vincent Lynch, and Michael J. Krische. 2000. "Nanostructured Polymer Duplexes via the Covalent Casting of 1-Dimensional H-Bonding Motifs: A New Strategy for the Self-Assembly of Macromolecular Precursors." *Journal of the American Chemical Society*. vol. 122, No. 20, pp. 5006-5007.

Ariga, Katsuhiko, Jun-ichi Kikuchi, Masanobu Naito, Emiko Koyama, and Norihiro Yamada. 2000. "Modulated Supramolecular Assemblies Composed of Tripeptide Derivatives: Formation of Micrometer-Scale Rods, Nanometer-Size Needles, and Regular Patterns with Molecular-Level Flatness from the Same Compound." *Langmuir*. vol. 16, No. 11, pp. 4929-4939.

Beniash, E., W. Traub, A. Veis, and S. Weiner. 2000. "A Transmission Electron Microscope Study Using Vitrified Ice Sections of Predentin: Structural Changes in the Dentin Collagenous Matrix Prior to Mineralization." *Journal of Structural Biology*. vol. 132, pp. 212-225.

Bigi, Adriana, Elisa Boanini, Silvia Panzavolta, and Norberto Roveri. 2000. "Biomimetic Growth of Hydroxyapatite on Gelatin Films Doped with Sodium Polyacrylate." *Biomacromolecules*. vol. 1, No. 4, pp. 752-756.

Bourel, Line, Olivier Carton, Hélène Gras-Masse, and Oleg Melnyk. 2000. "The Deprotection of Lys(Mtt) Revisited." *Journal of Peptide Science*. vol. 6, pp. 264-270.

Caplan, Michael R., Peter N. Moore, Shuguang Zhang, Roger D. Kamm, and Douglas A. Lauffenburger. 2000. "Self-Assembly of a β-Sheet Protein Governed by Relief of Electrostatic Repulsion Relative to van der Waals Attraction." *Biomacromolecules*. vol. 1, No. 4, pp. 627-631.

Cardullo, F., M. Crego Calama, B. H. M. Snellink-Ruël, J.-L. Weidmann, A Bielejewska, R. Fokkens, N. M. M. Nibbering, P. Timmerman, and D. N. Reinhoudt. 2000. "Covalent Capture of Dynamic Hydrogen-Bonded Assemblies." *Chem. Commun*. pp. 367-368.

Chamberlain, L. J., I. V. Yannas, H-P. Hsu, G. R. Strichartz, and M. Spector. 2000. "Near-Terminus Axonal Structure and Function Following Rat Sciatic Nerve Regeneration Through a Collagen-GAG Matrix in a Ten-Millimeter Gap." *Journal of Neuroscience Research*. vol. 60, pp. 666-677.

David, Sunil A., Satish K. Awasthi, and P. Balaram. 2000. "The Role of Polar and Facial Amphipathic Character in Determining Lipopolysaccharide-Binding Properties in Synthetic Cationic Peptides." *Journal of Endotoxin Research*. vol. 6, No. 3, pp. 249-256.

Dori, Yoav, Havazelet Bianco-Peled, Sushil K Satija, Gregg B. Fields, James B. McCarthy, and Matthew Tirrell. 2000. "Ligand Accessibility as Means to Control Cell Response to Bioactive Bilayer Membranes." *Journal of Biomedical Materials Research*. vol. 50, pp. 75-81.

Forns, Pilar, Janelle L. Lauer-Fields, Su Gao, and Gregg B. Fields. 2000. "Induction of Protein-Like Molecular Architecture by Monoalkyl Hydrocarbon Chains."*Biopolymers*. vol. 54, pp. 531-546.

Hisaeda, Yoshio, Eiji Ohshima, and Makiko Arimura. 2000. "Aggregation Behavior of Synthetic Peptide Lipids with Arginine in Aqueous Solution and Construction of a Vitamin $B_{12}$ Artifical Enzyme." *Colloids and Surfaces A: Physicochemical and Engineering Aspects*. bvl. 169, pp. 143-153.

Kogiso, Masaki, Yuji Okada, Takeshi Hanada, Kiyoshi Yase, and Toshimi Shimizu. 2000. "Self-Assembled Peptide Fibers from Valylvaline Bola-Amphiphiles by a Parallel 6-Sheet Network." *Biochimica et Biophysica Acta*. vol. 1475, pp. 346-352.

Langer, Robert. 2000. "Biomaterials in Drug Delivery and Tissue Engineering: One Laboratory's Experience." *Accounts of Chemical Research*. vol. 33, No. 2, pp. 94-101.

Liu, X. D., M. Skold, T. Umino, Y. K. Zhu, D. J. Romberger, J. R. Spurzem, and S. I. Rennard. 2000. "Endothelial Cell-Mediated Type I Collagen Gel Contraction Is Regulated by Hemin." *J. Lab. Clin. Med*. vol. 136, No. 2, pp. 100-109.

Lu, Lichun, Susan J. Peter, Michelle D. Lyman, Hui-Lin Lai, Susan M. Leite, Janet A. Tamada, Shiro Uyama, Joseph P. Vacanti, Robert Langer, and Antonios G. Mikos. 2000. "In Vitro and in Vivo Degradation of Porous Poly(DL-Lactic-*co*-Glycolic Acid) Foams." *Biomaterials*. bvl. 21, pp. 18371845.

Matsuura, T., R. Hosokawa, K. Okamoto, T. Kimoto, and Y. Akagawa. 2000. "Diverse Mechanisms of Osteoblast Spreading on Hydroxyapatite and Titanium."*Biomaterials*. vol. 21, pp. 1121-1127.

Ponticiello, Michael S., Robert M. Schinagl, Sudha Kadiyala, and Frank P. Barry. 2000. "Gelatin-Based Resorbable Sponge as a Carrier Matrix for Human Mesenchymal Stem Cells in Cartilage Regeneration Therapy." *Journal of Biomedical Materials Research*. vol. 52, pp. 246-255.

Powell, Sharon K., Jayashree Rao, Eva Roque, Motoyoshi Nomizu, Yuichiro Kuratomi, Yoshihiko Yamada, and Hynda K. Kleinman. 2000. "Neural Cell Response to Multiple Novel Sites on Laminin-1." *Journal of Neuroscience Research*. vol. 61, pp. 302-312.

Sakiyama-Elbert, Shelly E. and Jeffrey A. Hubbell. 2000. "Controlled Release of Nerve Growth Factor from a Heparin-Containing Fibrin-Based Cell Ingrowth Matrix." *Journal of Controlled Release*. vol. 69, pp. 149-158.

Sakiyama-Elbert, Shelly E. and Jeffrey A. Hubbell. 2000. "Development of Fibrin Derivatives for Controlled Release of Heparin-Binding Growth Factors." *Journal of Controlled Release*. vol. 65, pp. 389-402.

Thareja, R. K. and A. Mitra. 2000. "Random Laser Action in ZnO." *Appl. Phys*. vol. B 71, pp. 181-184.

Tunggal, Patrick, Neil Smyth, Mats Paulsson, and Mark-Christoph Ott. 2000. "Laminins: Structure and Genetic Regulation." *Microscopy Research and Technique*. vol. 51, pp. 214-227.

do Serro, Ana Paula Valagão Amadeu, Anabela Catarino Fernandes, and Benilde de Jesus Vieira Saramago. 2000. "Calcium Phosphate Deposition on Titanium Surfaces in the Presence of Fibronectin." *Journal of Biomedical Materials Research*. vol. 49, pp. 345-352.

Yamada, Norihiro and Katsuhiko Ariga. 2000. "Formation of β-Sheet Assemblage with a View to Developing an Amyloid Model." *Synlett*. vol. 5, pp. 575-586.

Yang, Lin and Paschalis Alexandridis. 2000. "Physicochemical Aspects of Drug Delivery and Release from Polymer-Based Colloids." *Current Opinion in Colloid & Interface Science*. vol. 5, pp. 132-143.

Yu, Huanran, Hiroshi Narusawa, Kisae Itoh, Akihiro Oshi, Narutoshi Yoshino, Kazuo Ohbu, Toshiaki Shirakawa, Kazuhiro Fukada, Masatoshi Fujii, Tadashi Kato, and Tsutomu Seimiya. 2000. "Hydrophilicity of Polar and Apolar Domains of Amphiphiles."*Journal of Colloid and Interface Science*. vol. 229, pp. 375-390.

Zhu, G., M. F. Mehler, P. C. Mabie, and J. A. Kessler. 2000. "Developmental Changes in Neural Progenitor Cell Lineage Commitment Do Not Depend on Epidermal Growth Factor Receptor Signaling" *Journal of Neuroscience Research*. vol. 59, pp. 312-320.

Orlic, Donald, Jan Kajstura, Stefano Chimenti, Igor Jakonuk, Stacie M. Anderson, Baosheng Li, James Picket, Ronald McKay, Bernardo Nadal-Ginard, David M. Bodine, Annarosa Leri, and Piero Anversa. Apr. 5, 2001. "Bone Marrow Cells Regenerate Infarcted Myocardium." *Nature*. vol. 410, pp. 701-705.

Vailhé, Bruno, Daniel Vittet, and Jean-Jacques Feige. Apr. 2001. "In Vitro Models of Vasculogenesis and Angiogenesis." *Laboratory Investigation*. vol. 81, No. 4, pp. 439-452.

Davis, N. G., J. Teisen, C. Schuh, and D. C. Dunand. May 2001. "Solid-State Foaming of Titanium by Superplastic Expansion of Argon-Filled Pores." *J. Mater. Res*. vol. 16, No. 5, pp. 1508-1519.

Rabchevsky, Alexander G. and George M. Smith. May 2001. "Therapeutic Interventions Following Mammalian Spinal Cord Injury." *Arch. Neurol*. vol. 58, pp. 721-726.

Huang, Michael H., Samuel Mao, Henning Feick, Haoquan Yan, Yiying Wu, Hannes Kind, Eicke Weber, Richard Russo, and Peidong Yang. Jun. 8, 2001. "Room-Temperature Ultraviolet Nanowire Nanolasers." *Science*. vol. 292, pp. 1897-1899.

Lee, Kuen Yong and David J. Mooney. Jul. 2001. "Hydrogels for Tissue Engineering." *Chemical Reviews*. vol. 101, No. 7, pp. 1869-1879.

Aggeli, A., I. A. Nyrkova, M. Bell, R. Harding, L. Carrick, T. C. B. McLeish, A. N. Semenov, and N. Boden. Oct. 9, 2001. "Hierarchical Self-Assembly of Chiral Rod-Like Molecules as a Model for Peptide β-Sheet Tapes, Ribbons, Fibrils, and Fibers." *Proceedings of the National Academy of Sciences of the United States of America*. vol. 98, No. 21, pp. 11857-11862.

Hartgerink, Jeffrey D., Elia Beniash, and Samuel I. Stupp. Nov. 23, 2001. "Self-Assembly and Mineralization of Peptide-Amphiphile Nanofibers." *Science*. vol. 294, pp. 1684-1688.

Richardson, Thomas P., Martin C. Peters, Alessandra B. Ennett, and David J. Mooney. Nov. 2001. "Polymeric System for Dual Growth Factor Delivery." *Nature Biotechnology*. vol. 19, pp. 1029-1034.

Mathew, Mathai and Shozo Takagi. Nov.-Dec. 2001. "Structures of Biological Minerals in Dental Research." *Journal of Research of the National Institute of Standards and Technology*. vol. 106, No. 6, pp. 1035-1044.

Woo, Byung Ho, Betsy F. Fink, Richard P., Jay A. Schrier, Yeong Woo Jo, Ge Jiang, Michelle DeLuca, Henry C. Vasconez, and Patrick P. DeLuca. Dec. 2001. "Enhancement of Bone Growth by Sustained Delivery of Recombinant Human Bone Morphogenetic Protein-2 in a Polymeric Matrix." *Pharmaceutical Research*. vol. 18, No. 12, pp. 1747-1753.

Barrère, F., P. Layrolle, C. A. Van Blitterswijk, and K. de Groot. 2001. "Biomimetic Coatings on Titanium: A Crystal Growth Study of Octacalciurn Phosphate." *Journal of Materials Science: Materials in Medicine*. vol. 12, pp. 529-534.

Bianco-Peled, Havazelet, Yoav Dori, James Schneider, Li-Piin Sung, Sushil Satija, and Matthew Tirrell. 2001. "Structural Study of Langmuir Monolayers Containing Lipidated Poly(ethylene glycol) and Peptides." *Langmuir*. vol. 17, No. 22, pp. 6931-6937.

Cavalli, M., G. Gnappi, A. Montenero, D. Bersani, P. P. Lottici, S. Kaciulis, G. Mattogno, and M. Fini. 2001. "Hydroxy- and Fluorapatite Films on Ti Alloy Substrates: Sol-gel Preparation and Characterization." *Journal of Materials Science*. vol. 36, pp. 3253-3260.

Chang, John C., Gregory J. Brewer, and Bruce C. Wheeler. 2001. "Modulation of Neural Network Activity by Patterning." *Biosensors & Bioelectronics*. vol. 16, pp. 527-533.

Chang, Sophia C. N., Jon A. Rowley, Geoffrey Tobias, Nicholas G. Genes, Amit K. Roy, David J. Mooney, Charles A. Vacanti, and Lawrence J. Bonassar. 2001. "Injection Molding of Chondrocyte/Alginate Constructs in the Shape of Facial Implants." *Journal of Biomedical Materials Research*. vol. 55, pp. 503-511.

Doi, Tomokiyo, Takatoshi Kinoshita, Hiroki Kamiya, Shintaro Washizu, Yoshiharu Tsujita, and Hiraoki Yoshimizu. 2001. "Aggregation of Polypeptide-Based Amphiphiles in Water." *Polymer Journal*. vol. 33, No. 2, pp. 160-164.

Gore, Tushar, Yoav Dori, Yeshayahu Talmon, Matthew Tirrell, and Havazelet Bianco-Peled. 2001. "Self-Assembly of Model Collagen Peptide Amphiphiles." *Langmuir*. vol. 17, No. 17, pp. 5352-5360.

Hoess, Ronald H. 2001. "Protein Design and Phage Display." *Chemical Reviews*. vol. 101, No. 10, pp. 3205-3218.

Huang, Eric J. and Louis F. Reichardt. 2001. "Neurotrophins: Roles in Neuronal Development and Function." *Annual Review of Neuroscience*. vol. 24, pp. 677-736.

Kam, L., W. Shain, J. N. Turner, and R. Bizios. 2001. "Axonal Outgrowth of Hippocampal Neurons on Micro-Scale Networks of Polylysine-Conjugated Laminin" *Biomaterials*. vol. 22, pp. 1049-1054.

Kikuchi, Masanori, Soichiro Itoh, Shizuko Ichinose, Kenichi Shinomiya, and Junzo Tanaka. 2001. "Self-Organization Mechanism in a Bone-Like Hydroxyapatite/Collagen Nancomposite Synthesized in Vitro and Its Biological Reaction in Vivo." *Biomaterials*. vol. 22, pp. 1705-1711.

Liu, Yuelian, Pierre Layrolle, Joost de Bruijn, Clemens van Blitterswijk, and Klaas de Groot. 2001. "Biomimetic Coprecipitation of Calcium Phosphate and Bovine Serum Albumin on Titanium Alloy." *Journal of Biomedical Materials Research*. vol. 57, pp. 327-335.

Look, D. C. 2001. "Recent Advances in ZnO Materials and Devices." *Materials Science and Engineering*. vol. B80, pp. 383-387.

Matsui, Hiroshi, and Gary E. Douberly, Jr. 2001. "Organization of Peptide Nanotubes into Macroscopic Bundles." *Langmuir*. vol. 17, No. 25, pp. 7918-7922.

Neet, K. E. and R. B. Campenot. 2001. "Receptor Binding, Internalization, and Retrograde Transport of Neurotrophic Factors." *CMLS, Cell Mol. Life Sci.* vol. 58, pp. 1021-1035.

Otsuka, Hidenori, Yukio Nagasaki, and Kazunori Kataoka. 2001. "Self-Assembly of Poly(ethylene glycol)—based Block Copolymers for Biomedical Applications." *Current Opinion in Colloid & Interface Science*. vol. 6, pp. 3-10.

Shimizu, Toshimi, Rika Iwaura, Mitsutoshi Masuda, Takeshi Hanada, and Kiyoshi Yase. 2001. "Internucleobase-Interaction-Directed Self-Assembly of Nanofibers from Homo- and Heteroditopic 1,ω-Nucleobase Bolaamphiphiles." *Journal of the American Chemical Society*. vol. 123, No. 25, pp. 5947-5955, S1-S16.

Socrates, George. 2001. *Infrared and Raman Characteristic Group Frequencies: Tables and Charts*. Third Edition. Chichester, England: John Wiley & Sons Ltd.

Spanos, Nikos and Petros G. Koutsoukos. 2001. "Model Studies of the Effect of Orthophospho-L-Serine on Biological Mineralization." *Langmuir*. vol. 17, No. 3, pp. 866-872.

Takadama, Hiroaki, Hyun-Min Kim, Tadashi Kokubo, and Takashi Nakamura. 2001. "TEM-EDX Study of Mechanism of Bonelike Apatite Formation on Bioactive Titanium Metal in Simulated Body Fluid." *Journal of Biomedical Materials Research*. vol. 57, pp. 441-448.

Tanihara, Masao, Yasuo Suzuki, Eriko Yamamoto, Atsushi Noguchi, and Yutaka Mizushima. 2001. "Sustained Release of Basic Fibroblast Growth Factor and Angiogenesis in a Novel Covalently Crosslinked Gel of Heparin and Alginate." *Journal of Biomedical Materials Research*. vol. 56, pp. 216-221.

Torchilin, Vladimir P. 2001. "Structure and Design of Polymeric Surfactant-Based Drug Delivery Systems." *Journal of Controlled Release*. vol. 73, pp. 137-172.

Yeung, C. K., L. Lauer, A. Offenhäusser, and W. Knoll. 2001. "Modulation of the Growth and Guidance of Rat Brain Stem Neurons Using Patterned Extracellular Matrix Proteins." *Neuroscience Letters*. vol. 301, pp. 147-150.

Zubarev, Eugene R., Martin U. Pralle, Eli D. Sone, and Samuel I. Stupp. 2001. "Self-Assembly of Dendron Rodcoil Molecules into Nanoribbons." *Journal of the American Chemical Society*. vol. 123, No. 17, pp. 4105-4106.

Hirschi, Karen K., Lihua Lai, Narasimhaswamy S. Belaguli, David A. Dean, Robert J. Schwartz, and Warren E. Zimmer. Feb. 22, 2002. "Transforming Growth Factor-β Induction of Smooth Muscle Cell Phenotype Requires Transcriptional and Post-transcriptional Control of Serum Response Factor." *The Journal of Biological Chemistry*. vol. 277, No. 8, pp. 6287-6295.

Xu, Weiming, Lizhi Liu, and Ian G. Charles. Feb. 2002. "Microencapsulated iNOS-expressing Cells Cause Tumor Suppression in Mice." *The FASEB Journal*. vol. 16, pp. 213-215.

Zubarev, Eugene R., Martin U. Pralle, Eli D. Sone, and Samuel I. Stupp. Feb. 2002. "Scaffolding of Polymers by Supramolecular Nanoribbons." *Advanced Materials*. vol. 14, No. 3, pp. 198-203.

Teng, Yang D., Erin B. Lavik, Xianlu Qu, Kook I. Park, Jitka Ourednik, David Zurakowski, Robert Langer, and Evan Y. Snyder. Mar. 5, 2002. "Functional Recovery Following Traumatic Spinal Cord Injury Mediated by a Unique Polymer Scaffold Seeded with Neural Stem Cells." *Proceedings of the National Academy of Sciences of the United States of America*. vol. 99, No. 5, pp. 3024-3029.

Bradbury, Elizabeth J., Lawrence D. F. Moon, Reena J. Popat, Von R. King, Gavin S. Bennett, Preena N. Patel, James W. Fawcett, and Stephen B. McMahon. Apr. 11, 2002. "Chondroitinase ABC Promotes Functional Recovery After Spinal Cord Injury." *Nature*. vol. 416, pp. 636-640.

Hartgerink, Jeffrey D., Elia Beniash, and Samuel I. Stupp. Apr. 16, 2002. "Supramolecular Chemistry and Self-Assembly Special Feature: Peptide-Amphiphile Nanofibers: A Versatile Scaffold for the Preparation of Self-Assembling Materials." *Proceedings of the National Academy of Sciences of the United States of America*. vol. 99, No. 8, pp. 5133-5138.

Vauthey, Sylvain, Steve Santoso, Haiyan Gong, Nicki Watson, and Shuguang Zhang. Apr. 16, 2002. "Molecular Self-Assembly of Surfactant-like Peptides to Form Nanotubes and Nanovesicles." *Proceedings of the National Academy of Sciences of the United States of America*. vol. 99, No. 8, pp. 5355-5360.

Nowak, Andrew P., Victor Breedveld, Lisa Pakstis, Bulent Ozbas, David J. Pine, Darrin Pochan, and Timothy J. Deming. May 23, 2002. "Rapidly Recovering Hydrogel Scaffolds from Self-Assembling Diblock Copolypeptide Amphiphiles." *Nature*. vol. 417, pp. 424-428.

GrandPré, Tadzia, Shuxin Li, and Stephen M. Strittmatter. May 30, 2002. "Nogo-66 Receptor Antagonist Peptide Promotes Axonal Regeneration." *Nature*. vol. 417, pp. 547-551.

Storch, Alexander and Johannes Schwarz. May 2002. "Neural Stem Cells and Neurodegeneration." *Current Opinion in Investigational Drugs*. vol. 3, No. 5, pp. 774-781.

Lendlein, Andreas and Robert Langer. May 31, 2002. "Biodegradable, Elastic Shape-Memory Polymers for Potential Biomedical Applications." *Science*. vol. 296, pp. 1673-1676.

Qiu, Jin, Dongming Cai, Haining Dai, Marietta McAttee, Paul N. Hoffman, Barbara S. Bregman, and Marie T. Filbin. Jun. 13, 2002. "Spinal Axon Regeneration Induced by Elevation of Cyclic AMP." *Neuron*. vol. 34, pp. 895-903.

Catledge, Shane A., Marc D. Fries, Yogesh K. Vohra, William R. Lacefield, Jack E. Lemons, Shauna Woodard, and Ramakrishna Venugopalan. Jun.-Aug. 2002. "Nanostructured Ceramics for Biomedical Implants." *Journal of Nanoscience and Nanotechnology*. vol. 2, No. 3/4, pp. 293-312.

Alsberg, Eben, Kenneth W. Anderson, Amru Albeiruti, Jon A. Rowley, and David J. Mooney. Sep. 17, 2002. "Engineering Growing Tissues." *Proceedings of the National Academy of Sciences of the United States of America*. vol. 99, No. 19, pp. 12025-12030.

Kay, Sarina, Anil Thapa, Karen M. Haberstroh, and Thomas J. Webster. Oct. 2002. "Nanostructured Polymer/Nanophase Ceramic Composites Enhance Osteoblast and Chondrocyte Adhesion." *Tissue Engineering*. vol. 8, No. 5, pp. 753-761.

Chang, Hua, Chester W. Brown, and Martin M. Matzuk. Dec. 2002. "Genetic Analysis of the Mammalian Transforming Growth Factor-β Superfamily." *Endocrine Reviews*. vol. 23, No. 6, pp. 787-823.

Busqué, Félix, Stephanie A. Hopkins, and Joseph P. Konopelski. 2002. "Progress Toward a Peptidomimetic of Laminin-Derived Pentapeptide YIGSR: Synthesis of the Unique Tricyclic Core Structure." *J. Org. Chem.* vol. 67, No. 17, pp. 6097-6103.

Canaple, Laurence, Annemie Rehor, and David Hunkeler. 2002. "Improving Cell Encapsulation Through Size Control." *J. Biomater. Sci. Polymer Edn.* vol. 13, No. 7, pp. 783-796.

Caplan, Michael R, Elissa M. Schwartzfarb, Shuguang Zhang, Roger D. Kamm, and Douglas A. Lauffenburger. 2002. "Control of Self-Assembling Oligopeptide Matrix Formation Through Systematic Variation of Amino Acid Sequence." *Biomaterials*. vol. 23, pp. 219-227.

Chen, Zhi Jiang, Yvonne Ughrin, and Joel M. Levine. 2002. "Inhibition of Axon Growth by Oligodendrocyte Precursor Cells." *Molecular and Cellular Neuroscience*. vol. 20, pp. 125-139.

Cornish, Toby, Darren W. Branch, Bruce C. Wheeler, and James T. Campanelli. 2002. "Microcontact Printing: A Versatile Technique for the Study of Synaptogenic Molecules." *Molecular and Cellular Neuroscience*. vol. 20, pp. 140-153.

Costa, Silvia, Thierry Planchenault, Cecile Charriere-Bertrand, Yann Mouchel, Christiane Fages, Sharon Juliano, Thierry Lefrançois, Georgia Barlovatz-Meimon, and Marcienne Tardy. 2002. "Astroglial Permissivity for Neuritic Outgrowth in Neuron-Astrocyte Cocultures Depends on Regulation of Laminin Bioavailability." *GLIA*. vol. 37, pp. 105-113.

Gariépy, Jean, Sandrine Rémy, Xiuguo Zhang, James R. Ballinger, Eleonora Bolewska-Pedyczak, Michael Rauth, and Stuart K. Bisland. 2002. "A Simple Two-Step Approach for Introducing a Protected Diaminedithiol Chelator During Solid-Phase Assembly of Peptides." *Bioconjugate Chem.* vol. 13, No. 3, pp. 679-684.

Glättli, Alice, Xavier Daura, Dieter Seebach, and Wilfred F. van Gunsteren. 2002. "Can One Derive the Confrontational Preference of a β-Peptide from Its CD Spectrum?" *Journal of the American Chemical Society*. vol. 124, No. 44, pp. 12972-12978.

Gutwein, Luke G. and Thomas J. Webster. 2002. "Osteoblast and Chrondrocyte Proliferation in the Presence of Alumina and Titania Nanoparticles." *Journal of Nanoparticle Research*. vol. 4, pp. 231-238.

Huang, Ning-Ping, Gabor Csucs, Kazunori Emoto, Yukio Nagasaki, Kazunori Kataoka, Marcus Textor, and Nicholas D. Spencer. 2002. "Covalent Attachment of Novel Poly(ethylene glycol)—Poly(DL-lactic acid) Copolymeric Micelles to $TiO_2$ Surfaces." *Langmuir*. vol. 18, No. 1, pp. 252-258.

Issac, Roy and Jean Chmielewski. 2002. "Approaching Exponential Growth with a Self-Replicating Peptide." *Journal of the American Chemical Society*. vol. 124, No. 24, pp. 6808-6809.

Joshi, Mital and Michael G. Fehlings. 2002. "Development and Characterization of a Novel, Graded Model of Clip Compressive Spinal Cord Injury in the Mouse: Part 1. Clip Design, Behavioral Outcomes, and Histopathology." *Journal of Neurotrauma*. vol. 19, No. 2, pp. 175-190.

Joshi, Mital and Michael G. Fehlings. 2002. "Development and Characterization of a Novel, Graded Model of Clip Compressive Spinal Cord Injury in the Mouse: Part 2. Quantitative Neuroanatomical Assessment and Analysis of the Relationships Between Axonal Tracts, Residual Tissue, and Locomotor Recovery." *Journal of Neurotrauma*. vol. 19, No. 2, pp. 191-203.

Kruger, Ryan G., Patrick Dostal, and Dewey G. McCafferty. 2002. "An Economical and Preparative Orthogonal Solid Phase Synthesis of Fluorescein and Rhodamine Derivatized Peptides: FRET Substrates for the *Staphylococcus aureus* Sortase SrtA Transpeptidase Reaction." *Chem. Commun.* pp. 2092-2093.

Lauer, L., A. Vogt, C. K. Yeung, W. Knoll, and A. Offenhäusser. 2002. "Electrophysiological Recordings of Patterned Rat Brain Stem Slice Neurons." *Biomaterials*. vol. 23, pp. 3123-3130.

Lavik, Erin, Yang D. Teng, Evan Snyder, and Robert Langer. 2002. "Speeding Neural Stem Cells on Scaffolds of PGA, PLA, and Their Copolymers." *Methods in Molecular Biology: Neural Stem Cells: Methods and Protocols*. vol. 198, pp. 89-97.

Marini, Davide M., Wonmuk Hwang, Douglas A. Lauffenburger, Shuguang Zhang, and Roger D. Kamm. 2002. "Left-Handed Helical Ribbon Intermediates in the Self-Assembly of a β-Sheet Peptide." *Nano Letters*. vol. 2, No. 4, pp. 295-299.

Ohsaki, Mio, Tatsuya Okuda, Akihiro Wada, Toshiya Hirayania, Takuro Niidome, and Haruhiko Aoyagi. 2002. "In Vitro Gene Transfection Using Dendritic Poly(L-lysine)." *Bioconjugate Chem.* vol. 13, No. 3, pp. 510-517.

Okano, Hideyuki. 2002. "Stem Cell Biology of the Central Nervous System." *Journal of Neuroscience Research*. vol. 69, pp. 698-707.

Parmar, Malin, Charlotta Skogh, Anders Björklund, and Kenneth Campbell. 2002. "Regional Specification of Neurosphere Cultures Derived from Subregions of the Embryonic Telencephalon." *Molecular and Cellular Neuroscience*. vol. 21, pp. 645-656.

Porter, A. E., L. W. Hobbs, V. Benezra Rosen, and M. Spector. 2002. "The Ultrastructure of the Plasma-Sprayed Hydroxyapatite-bone Interface Predisposing to Bone Bonding." *Biomaterials*. vol. 23, pp. 725-733.

Rowley, Jon A. and David J. Mooney. 2002. "Alginate Type and RGD Density Control Myoblast Phenotype." *Journal of Biomedical Materials Research*. vol. 60, pp. 217-223.

Santoso, Steve S., Sylvain Vauthey, and Shuguang Zhang. 2002. "Structures, Function and Applications of Amphiphilic Peptides." *Current Opinion in Colloid & Interface Science*. vol. 7, pp. 262-266.

Thiébaud, Pierre, Lars Lauer, Wolfgang Knoll, and Andreas Offenhäuser. 2002. "PDMS Device for Patterned Application of Microfluids to Neuronal Cells Arranged by Microcontact Printing." *Biosensors & Bioelectronics*. vol. 17, pp. 87-93.

Tryoen-Tóth, Petra, Dominique Vautier, Youssef Haikel, Jean-Claude Voegel, Pierre Schaaf, Johanna Chluba, and Joelle Ogier. 2002. "Viability, Adhesion, and Bone Phenotype of Osteoblast-like Cells on Polyelectrolyte Multilayer Films." *Journal of Biomedical Materials Research*. vol. 60, pp. 657-667.

Young, Wise. 2002. "Spinal Cord Contusion Models." *Progress in Brain Research*. vol. 137, pp. 231-255.

Lutolf, Matthias P., Franz E. Weber, Hugo G. Schmoekel, Jason C. Schense, Thomas Kohler, Ralph Müller, and Jeffrey A. Hubbell. May 2003. "Repair of Bone Defects Using Synthetic Mimetics of Collagenous Extracellular Matrices." *Nature Biotechnology*. vol. 21, pp. 513-518.

Shaw, Derek and Molly S. Shoichet. May 2003. "Toward Spinal Cord Injury Repair Strategies: Peptide Surface Modification of Expanded Poly(Tetrafluoroethylene) Fibers for Guided Neurite Outgrowth in Vitro." *The Journal of Craniofacial Surgery*. vol. 14, No. 3, pp. 308-316.

Cheng, Hongwei, Wei Jiang, Frank M. Phillips, Rex C. Haydon, Ying Peng, Lan Zhou, Hue H. Luu, Naili An, Benjamin Breyer, Pantila Vanichakarn, Jan Paul Szatkowski, Jae Yoon Park, and Tong-Chuan He. Aug. 2003. "Osteogenic Activity of the Fourteen Types of Human Bone Morphogenetic Proteins (BMPs)." *The Journal of Bone & Joint Surgery*. vol. 85-A, No. 8, pp. 1544-1552, 141.

Pavlov, Georges, Stéphanie Finet, Karine Tatarenko, Evgueniya Komeeva, and Christine Ebel. 2003. "Conformation of Heparin Studied with Macromolecular Hydrodynamic Methods and X-ray Scattering." *Eur. Biophys. J.* vol. 32, pp. 437-449.

Arinzeh, Treena Livingston, Susan J. Peter, Michael P. Archambault, Christian van den Bos, Steve Gordon, Karl Kraus, Alan Smith, and Sudha Kadiyala. Oct. 2003. "Allogeneic Mesenchymal Stem Cells Regenerate Bone in a Critical-Sized Canine Segmental Defect." *The Journal of Bone & Joint Surgery*. vol. 85-A, No. 10, pp. 1927-1935.

Zhang, Shuguang. Oct. 2003. "Fabrication of Novel Biomaterials Through Molecular Self-Assembly." *Nature Biotechnology*. vol. 21, No. 10, pp. 1171-1178.

Aggeli, Amalia, Mark Bell, Lisa M. Carrick, Colin W. G. Fishwick, Richard Harding, Peter J. Mawer, Sheena E. Radford, Andrew E. Strong, and Neville Boden. 2003. "pH as a Trigger of Peptide β-Sheet Self-Assembly and Reversible Switching Between Nematic and Isotropic Phases." *Journal of the American Chemical Society*. vol. 125, No. 32, pp. 9619-9628.

Alsina, Jordi and Fernando Albericio. 2003. "Solid-Phase Synthesis of C-Terminal Modified Peptides." *Biopolymers (Peptide Science)*. vol. 71, pp. 454-477.

Anthony, Shawn G. 2003. "Injectable Biomaterials for Bone Tissue Engineering.".

Boontheekul, Tanyanit and David J. Mooney. 2003. "Protein-Based Signaling Systems in Tissue Engineering." *Current Opinion in Biotechnology*. vol. 14, pp. 559-565.

Fauza, Dario O. 2003. "Tissue Engineering: Current State of Clinical Application." *Current Opinion in Pediatrics*. vol. 15, pp. 267-271.

Ganesh, S. and R. Jayakumar. 2003. "Structural Transitions Involved in a Novel Amyloid-Like β-Sheet Assemblage of Tripeptide Derivatives." *Biopolymers*. vol. 70, pp. 336-345.

Ganesh, S., S. Prakash, and R. Jayakumar. 2003. "Spectroscopic Investigation on Gel-Forming β-Sheet Assemblage of Peptide Derivatives." *Biopolymers*. vol. 70, pp. 346-354.

Gergely, C. S., P. Bar Yosef, R. Govrin-Lippman, F. Cuisinier, and H. Füredi-Milhofer. 2003. "The Deposition of Calcium Phosphates Within Polyelectrolyte Multilayer Films." *Key Engineering Materials*. vols. 240-242 (Bioceramics), pp. 287-290.

Goeden-Wood, Nichole L., Jay D. Keasling, and Susan J. Muller. 2003. "Self-Assembly of a Designed Protein Polymer into β-Sheet Fibrils and Responsive Gels." *Macromolecules*. vol. 36, No. 8, pp. 2932-2938.

Ishihara, Masayuki, Kiyohaya Obara, Toshiaki Ishizuka, Masanori Fujita, Masato Sato, Kazunori Masuoka, Yoshio Saito, Hirofumi Yura, Takemi Matsui, Hidemi Hattori, Makoto Kikuchi, and Akira Kurita. 2003. "Controlled Release of Fibroblast Growth Factors and Heparin from Photocrosslinked Chitosan Hydrogels and Subsequent Effect on in Vivo Vascularization." *Journal of Biomedical Materials Research*. vol. 64A, pp. 551-559.

Malkar, Navdeep B., Janelle L. Lauer-Fields, Darius Juska, and Gregg B. Fields. 2003. "Characterization of Peptide-Amphiphiles Possessing Cellular Activation Sequences." *Biomacromolecules*. vol. 4, No. 3, pp. 518-528.

Niece, Krista L., Jeffrey D. Hartgerink, Jack J. J. M. Donners, and Samuel I. Stupp. 2003. "Self-Assembly Combining Two Bioactive Peptide-Amphiphile Molecules into Nanofibers by Electrostatic Attraction." *Journal of the American Chemical Society*. vol. 125, No. 24, pp. 7146-7147.

Steward, Oswald, Binhai Zheng, and Marc Tessier-Lavigne. 2003. "False Resurrections: Distinguishing Regenerated from Spared Axons in the Injured Central Nervous System." *The Journal of Comparative Neurology*. vol. 459, pp. 1-8.

Wu, Sufan, Yoshihisa Suzuki, Yoko Ejiri, Toni Noda, Hongliang Bai, Masaaki Kitada, Kazuya Kataoka, Masayoshi Ohta, Hirotomi Chou, and Chizuka Ide. 2003. "Bone Marrow Stromal Cells Enhance Differentiation of Cocultured Neurosphere Cells and Promote Regeneration of Injured Spinal Cord." *Journal of Neuroscience Research*. vol. 72, pp. 343-351.

Yamada, Norihiro, Tsukasa Komatsu, Hirotsugu Yoshinaga, Kayo Yoshizawa, Susumu Edo, and Masashi Kunitake. 2003. "Self-Supporting Elastic Film without Covalent Linkages as a Hierarchically Integrated β-Sheet Assembly." *Angew. Chem. Int. Ed*. vol. 42, pp. 5496-5499.

Zhang, Yan, Hongwei Gu, Zhimou Yang, and Bing Xu. 2003. "Supramolecular Hydrogels Respond to Ligand-Receptor Interaction." *Journal of the American Chemical Society*. vol. 125, No. 45, pp. 13680-13681.

Hirano, Yoshiaki and David J. Mooney. Jan. 5, 2004. "Peptide and Protein Presenting Materials for Tissue Engineering." *Advanced Materials*. vol. 16, No. 1, pp. 17-25.

Silva, Gabriel A., Catherine Czeisler, Krista L. Niece, Elia Beniash, Daniel A. Harrington, John A. Kessler, and Samuel I. Stupp. Feb. 27, 2004. "Selective Differentiation of Neural Progenitor Cells by High-Epitope Density Nanofibers." *Science*. vol. 303, pp. 1352-1355.

Faulkner, Jill R., Julia E. Herrmann, Michael J. Woo, Keith E. Tansey, Ngan B. Doan, and Michael V. Sofroniew. Mar. 3, 2004. "Reactive Astrocytes Protect Tissue and Preserve Function after Spinal Cord Injury." *The Journal of Neuroscience*. vol. 24, No. 9, pp. 2143-2155.

Cao, Renhai, Anna Eriksson, Hajime Kubo, Kari Alitalo, Yihai Cao, Johan Thyberg. Mar. 19, 2004. "Comparative Evaluation of FGF-2-, VEGF-A-, and VEGF-C-Induced Angiogenesis, Lymphangiogenesis, Vascular Fenestrations, and Permeability." *Circulation Research*. vol. 94, pp. 664-670.

Anthony, Shawn G. Mar. 28-Apr. 1, 2004. "Self-Assembling Nanofiber Matrix for Bone Regeneration." *The 227th ACS National Meeting*. Anaheim, CA.

Donners, Jack J. J. M. Mar. 28-Apr. 1, 2004. "Growth Factor Binding Self-Assembling Nanofiber Networks for Tissue Regeneration." *The 227th ACS National Meeting*. Anaheim, CA.

Nikulina Elena, J. Lille Tidwell, Hai Ning Dai, Barbara S. Bregman, and Marie T. Filbin. Jun. 8, 2004. "The Phosphodiesterase Inhibitor Rolipram Delivered after a Spinal Cord Lesion Promotes Axonal Regeneration and Functional Recovery." *Proceedings of the National Academy of Sciences of the United States of America*. vol. 101, No. 23, pp. 8786-8790.

Pearse, Damien D., Francisco C. Pereira, Alexander E. Marcillo, Margaret L. Bates, Yerko A. Berrocal, Marie T. Filbin, and Mary Bartlett Bunge. Jun. 2004. "cAMP and Schwann Cells Promote Axonal Growth and Functional Recovery After Spinal Cord Injury." *Nature Medicine*. vol. 10, No. 6, pp. 610-616.

Lu, Paul, Hong Yang, Leonard L. Jones, Marie T. Filbin, and Mark H. Tuszynski. Jul. 14, 2004. "Combinatorial Therapy with Neurotrophins and cAMP Promotes Axonal Regeneration beyond Sites of Spinal Cord Injury." *The Journal of Neuroscience*. vol. 24, No. 28, pp. 6402-6409.

Lee, K. W., J. J. Yoon, J. H. Lee, S. Y. Kim, H. J. Jung, S. J. Kim, J. W. Joh, H. H. Lee, D. S. Lee, and S. K. Lee. 2004. "Sustained Release of Vascular Endothelial Growth Factor From Calcium-Induced Alginate Hydrogels Reinforced by Heparin and Chitosan." *Transplantation Proceedings*. vol. 36, pp. 2464-2465.

Matsumura, Sachiko, Shinobu Uemura, and Hisakazu Mihara. 2004. "Fabrication of Nanofibers with Uniform Morphology by Self-Assembly of Designed Peptides." *Chem. Eur. J*. vol. 10, pp. 2789-2794.

Sieminski, A. L., R. P. Hebbel, and K. J. Gooch. 2004. "The Relative Magnitudes of Endothelial Force Generation and Matrix Stiffness Modulate Capillary Morphogenesis in Vitro." *Experimental Cell Research*. vol. 297, pp. 574-584.

Vandermeulen, Guido W. M. and Harm-Anton Klok. 2004. "Peptide/Protein Hybrid Materials: Enhanced Control of Structure and Improved Performance through Conjugation of Biological and Synthetic Polymers." *Macromolecular Bioscience*. vol. 4, pp. 383-398.

Wang, Lin-Fa and Meng Yu. 2004. "Epitope Identification and Discovery Using Phage Display Libraries: Applications in Vaccine Development and Diagnostics." *Current Drug Targets*. vol. 5, No. 1, pp. 1-15.

Sayle, Roger. Printed Nov. 9, 2005. "Physiological Ionization and pKa Prediction." http://www.daylight.com/meetings/emug00/Sayle/pkapredict.html. pp. 1-13.

Bull, Steve R., Mustafa O. Guler, Rafael E. Bras, Thomas J. Meade, and Samuel I. Stupp. 2005. "Self-Assembled Peptide Amphiphile Nanofibers Conjugated to MRI Contrast Agents." *Nano Letters*. vol. 5, No. 1, pp. 1-4.

Guler, Mustafa O., Stephen Soukasene, James F. Hulvat, and Samuel I. Stupp. 2005. "Presentation and Recognition of Biotin on Nanofibers Formed by Branched Peptide Amphiphiles." *Nano Letters*. vol. 5, No. 2, pp. 249-252.

Loudon, M. "Amino Acid Structures at Physiological pH." Printed Jun. 5, 2006. www.brynmawr.edu/Acads/Chem/mnerzsto/amino_acids.htm, amino_acids_2.gif, and amino_acids3.htm.

Nomizu, Motoyoshi, Keizo Yamamura, Hynda K. Kleinman, and Yoshihiko Yamada. Aug. 1, 1993. "Multimeric Forms of Tyr-Ile-Gly-Ser-Arg (YIGSR) Peptide Enhance the Inhibition of Tumor Growth and Metastasis." *Cancer Research*. vol. 53, pp. 3459-3461.

Jin, Young-Gu and K. J. Chang. Feb. 26, 2001. "Mechanism for the Enhanced Diffusion of Charged Oxygen Ions in $SiO_2$." *Physical Review Letters*. vol. 86, No. 9, pp. 1793-1796.

Matsui, Hiroshi and Robert MacCuspie. Dec. 2001. "Metalloporphyrin Nanotube Fabrication Using Peptide Nanotubes as Templates." *Nano Letters*. vol. 1, No. 12, pp. 671-675.

Irvine, Darrell J. and Anne M. Mayes. 2001. "Nanoscale Clustering of RGD Peptides at Surfaces Using Comb Polymers. 1. Synthesis and Characterization of Comb Thin Films." *Biomacromolecules*. vol. 2, No. 1, pp. 85-94.

Matsui, Hiroshi, Precila Porrata, and Gary E. Douberly, Jr. 2001. "Protein Tubule Immobilization on Self-Assembled Monolayers on Au Substrates." *Nano Letters*. vol. 1, No. 9, pp. 461-464.

Slocik, Joseph M., Joshua T. Moore, and David W. Wright. Mar. 2002. Monoclonal Antibody Recognition of Histidine-Rich Peptide Encapsulated Nanoclusters. *Nano Letters*. vol. 2, No. 3, pp. 169-173.

Shih, Sheng-Ming, Wei-Fang Su, Yuh-Jiuan Lin, Cen-Shawn Wu, and Chii-Dong Chen. 2002. "Two-Dimensional Arrays of Self-Assembled Gold and Sulfur-Containing Fullerene Nanoparticles." *Langmuir*. vol. 18, No. 8, pp. 3332-3335.

Wong, Michael S., Jennifer N. Cha, Kyoung-Shin Choi, Timothy J. Deming, and Galen D. Stucky. 2002. "Assembly of Nanoparticles into Hollow Spheres Using Block Copolypeptides." *Nano Letters*. vol. 2, No. 6, pp. 583-587.

"AccessScience Search Results. Amphiphile." Accessed online May 7, 2007. http://www.accessscience.com/search/asearch?location=titlestext&newSearch=1&pubpriv=private&categories=dictionary&categval=dictionary&text=amphiphile. McGraw-Hill Encyclopedia of Science & Technology Online.

Jackowski, Andre. 1995. "Neural Injury Repair: Hope for the Future as Barriers to Effective CNS Regeneration Become Clearer." J. Neurosurg. vol. 9, pp. 303-317.

Knake, Rene, Amir W. Fahmi, Syed A. M. Tofail, Jason Clohessy, Miroslav Mihov, and Vincent J. Cunnane. 2005. "Electrochemical Nucleation of Gold Nanoparticles in a Polymer Film at a Liquid-Liquid Interface." Langmuir. vol. 21, No. 3, pp. 1001-1008.

Nomizu, Motoyoshi, Atsushi Utani, Norio Shiraishi, Maura C. Kibbey, Yoshihiko Yamada, and Peter P. Roller. Jul. 15, 1992. "The All-D-Configuration Segment Containing the IKVAV Sequence of Laminin A Chain Has Similar Activities to the All-L-Peptide in Vitro and in Vivo." The Journal of Biological Chemistry. vol. 267, No. 20, pp. 14118-14121.

Margomenou-Leonidopoulou, G. 1994. "Thermotropic Mesophases of Ionic Amphiphiles. II. Ionic Amphiphiles in Aqueous Media." Journal of Thermal Analysis. vol. 42, pp. 1041-1061.

Rappolt, Michael and Gert Rapp. 1996. "Structure of the Stable and Metastable Ripple Phase of Dipalmitoylphosphatidylcholine." Eur. Biophys. J. vol. 24, pp. 381-386.

Goveas, J. L. and S. T. Milner, 1997. "Dynamics of the Lamellar—Cylindrical Transition in Weakly Segregated Diblock Copolymer Melts." Macromolecules. vol. 30, No. 9, pp. 2605-2612.

Munson, John B. and Stephen B. McMahon. 1997. "Effects of GDNF on Axotomized Sensory and Motor Neurons in Adult Rats." European Journal of Neuroscience. vol. 9, pp. 1126-1129.

Fernandez, A., M. A. Alsina, I. Haro, R. Galantai, and F. Reig. 1998. "Synthesis and Physicochemical Characterization of Cyclic Laminin Related Peptides." Langmuir. vol. 14, No. 13, pp. 3625-3630.

Yagi, Nobuhiro, Yoshikatsu Ogawa, Masato Kodaka, Tomoko Okada, Takenori Tomohiro, Takeo Konakahara, and Hiroaki Okuno. 1999. "A Surface-Modified Functional Liposome Capable of Binding to Cell Membranes." Chem. Commun. pp. 1687-1688.

Luo, Yi and Glenn D. Prestwich. 2001. "Novel Biomaterials for Drug Delivery." Expert Opin. Ther. Patents. vol. 11, No. 9, pp. 1395-1410.

Marchi-Artzner, Valerie, Barbara Lorz, Ulrike Hellerer, Martin Kantlehner, Horst Kessler, and Erich Sackmann. 2001. "Selective Adhesion of Endothelial Cells to Artificial Membranes with a Synthetic RGD-Lipopeptide." Chem. Eur. J. vol. 7, No. 5, pp. 1095-1101.

Blight, Andrew R. Nov. 2002. "Miracles and Molecules—Progress in Spinal Cord Repair." Nature Neuroscience Supplement. vol. 5, pp. 1051-1054.

Rodger, Alison, Jascindra Rajendra, Rachel Marrington, Malin Ardhammar, Bengt Norden, Jonathan D. Hirst, Andrew T. B. Gilbert, Timothy R. Dafforn, David J. Halsall, Cheryl A. Woolhead, Colin Robinson, Teresa J. T. Pinheiro, Jurate Kazlauskaite, Mark Seymour, Niuvis Perez, and Michael J. Hannon. 2002. "Flow Oriented Linear Dichroism to Probe Protein Orientation in Membrane Environments." Phys. Chem. Chem. Phys. vol. 4, pp. 4051-4057.

Silva, G. A., K. L. Kehl, K. L. Niece, and S. I. Stupp. May 4, 2003. "Nanoengineered Peptide Amphiphile Network for Photoreceptor Replacement in Degenerative Retinal Disorders." Investigative Ophthalmology & Visual Science. Abstract No. 492 from Annual Meeting of the Association for Research in Vision and Opthalmology.

Brandenburg, Klaus, Frauke Wagner, Mareike Muller, Holger Heine, Jorg Andra, Michel H. J. Koch, Ulrich Zahringer, and Ulrich Sydel. 2003. "Physicochemical Characterization and Biological Activity of a Glycoglycerolipid from Mycoplasma fermentans." Eur. J. Biochem. vol. 270, pp. 3271-3279.

Czeisler, C V. M. Tysseling-Mattiace, G. A. Silva, S. I. Stupp, and J. A. Kessler. 2003. "Behavoral Improvement and Increased Survival Rate after Treatment with a Self Assembling Gel in a Rat Model of Spinal Cord Injury." 2003 Abstract Viewer/Itinerary Planner. Program No. 245.22. Washington, DC: Society for Neuroscience. Printed Feb. 5, 2007. p. 1. http://sfn.scholarone.com/itin2003/main.html?new_page_id=126&abstract_id=1554.

Schmidt, Christine E. and Jennie Baler Leach. 2003. "Neural Tissue Engineering: Strategies for Repair and Regeneration." Annu. Rev. Biomed. Eng. vol. 5, pp. 293-347.

t' Hart, Bert A. and Sandra Amor. 2003. "The Use of Animal Models to Investigate the Pathogenesis of Neuroinflammatory Disorders of the Central Nervous System." Current Opinion in Neurology. vol. 16, pp. 375-383.

Beniash, Elia, Jeffery D. Hartgerink, Hannah Storrie, John C. Stendahl, and Samuel I. Stupp. 2005. "Self-Assembling Peptide Amphiphile Nanofiber Matrices for Cell Entrapment." Acta Biomaterialia. vol. 1, pp. 387-397.

Hoke, Ahmet. Aug. 2006. "Mechanisms of Disease: What Factors Limit the Success of Peripheral Nerve Regeneration in Humans?" Nature Clinical Practice Neurology. vol. 2, No. 8, pp. 448-454.

Kokkoli, Efrosini, Anastasia Mardilovich, Alison Wedekind, Emilie L. Rexeisen, Ashish Garg, and Jennifer A. Craig. 2006. "Self-Assembly and Applications of Biomimetic and Bioactive Peptide-Amphiphiles." Soft Matter. vol. 2, pp. 1015-1024.

The LabRat.com. 2007, updated. Hank's Buffered Salt Solution (HBSS) Recipe. http://www.thelabrat.com/protocolsHanks.shtml. Printed Jan. 19, 2007. pp. 1-2.

Tam, James P. 1996. "Recent Advances in Multiple Antigen Peptides." Journal of Immunological Methods. vol. 196, pp. 17-32.

Merkler, Doron, Gerlinde A. S. Metz, Olivier Raineteau, Volker Dietz, Martin E. Schwab, and Karim Fouad. May 15, 2001. "Locomotor Recovery in Spinal Cord-Injured Rats Treated with an Antibody Neutralizing the Myelin-Associated Neurite Growth Inhibitor Nogo-A." The Journal of Neuroscience. vol. 21, No. 10, pp. 3665-3673.

Bonnet, Dominique, Kader Thiam, Estelle Loing, Oleg Melnyk, and Hélène Gras-Masse. 2001. Synthesis by Chemoselective Ligation and Biological Evaluation of Novel Cell-Permeable PKC-ξ Pseudosubstrate Lipopeptides. J. Med. Chem. vol. 44, No. 3, pp. 468-471.

Grothe, Claudia and Guido Nikkhah. 2001. "The role of Basic Fibroblast Growth Factor in Peripheral Nerve Regeneration." Anat. Embryol. vol. 204, pp. 171-177.

Silva, G. A., C. Czeisler, K. L. Niece, E. Beniash, J. D. Hartgerink, J. A. Kessler, and S. I. Stupp. Nov. 2-7, 2002. "Development of Neural Progenitor Cells Encapsulated in a Peptide Amphiphile Substrate That Is Induced to Self-Assemble Under Physiological Conditions." Biosis. Society for Neuroscience Abstract Viewer and Itinerary Planner—2002. Abstract No. 825.4. 32nd Annual Meeting of the Society for Neuroscience; Orlando, Florida.

Leng, J., S. U. Egelhaaf, and M. E. Cates. Sep. 2003. "Kinetics of the Micelle-to-Vesicle Transition: Aqueous Lecithin-Bile Salt Mixtures." Biophysical Journal. vol. 85, No. 3, pp. 1624-1646.

Kibbey, Maura C., Mathias Jucker, Benjamin S. Weeks, Rachael L. Neve, Wiliam E. Van Nostrand, and Hynda K. Kleinman. Nov. 1993. "β-Amyloid Precursor Protein Binds to the Neurite-Promoting IKVAV Site of Laminin." Proc. Natl. Acad. Sci. U.S.A. vol. 90, pp. 10150-10153.

Oka, Kazunari, Masaaki Yamamoto, Toshiharu Nonaka, and Masamichi Tomonaga. Apr. 1996. "The Significance of Artificial Cerebrospinal Fluid as Perfusate and Endoneurosurgery." Neurosurgery Online. vol. 38, No. 4, pp. 733-736.

Rapaport, Hanna, Kristian Kjaer, Torben R. Jensen, Leslie Leiserowitz, and David A. Tirrell. 2000. "Two-Dimensional Order in β-Sheet Peptide Monolayers." Journal of the American Chemical Society. vol. 122, No. 50, pp. 12523-12529.

Avrahami, Dorit and Yechiel Shai. 2002. "Conjugation of a Magainin Analogue with Lipophilic Acids Controls Hydrophobicity, Solution Assembly, and Cell Selectivity." Biochemistry. vol. 41, No. 7, pp. 2254-2263.

Yamada, Masanori, Yuichi Kadoya, Shingo Kasai, Kozue Kato, Mayumi Mochizuki, Norio Nishi, Nobuhisa Watanabe, Hynda K. Kleinman, Yoshihiko Yamada, and Motoyoshi Nomizu. 2002. "Ile-Lys-Val-Ala-Val (IKVAV)-Containing Laminin α1 Chain Peptides Form Amyloid-like Fibrils." FEBS Letters. vol. 530, pp. 48-52.

McGregor, Clare-Louise, Lu Chen, Neil C. Pomroy, Peter Hwang, Sandy Go, Avijit Chakrabartty, and Gilbert G. Privé. Feb. 2003. "Lipopeptide Detergents Designed for the Structural Study of Membrane Proteins." Nature Biotechnology. vol. 21, pp. 171-176.

Ohmori, Hideya, Yasumitsu Sato, and Akiyoshi Namiki. 2004. "The Anticonvulsant Action of Propofol on Epileptiform Activity in Rat Hippocampal Slices." Anesth. Analg. vol. 99, pp. 1095-1101.

Shahraki, Ali and Trevor W. Stone. 2004. "Blockade of Presynaptic Adenosine A1 Receptor Responses by Nitric Oxide and Superoxide in Rat Hippocampus." European Journal of Neuroscience. vol. 20, pp. 719-728.

Sone, Eli D. and Samuel I. Stupp. 2004. "Semiconductor-Encapsulated Peptide-Amphiphile Nanofibers." Journal of the American Chemical Society. vol. 126, No. 40, pp. 12756-12757.

Smith, L. A. and P. X. Ma. 2004. "Nano-Fibrous Scaffolds for Tissue Engineering." Colloids and Surfaces. B: Biointerfaces. vol. 39, pp. 125-131.

Tsonchev, Stefan, George C. Schatz, and Mark A. Ratner. 2004. "Electrostatically-Directed Self-Assembly of Cylindrical Peptide Amphiphile Nanostructures." J. Phys. Chem. B. vol. 108, No. 26, pp. 8817-8822.

Tsonchev, Stefan, Alessandro Troisi, George C. Schatz, and Mark A. Ratner. 2004. "All-Atom Numerical Studies of Self-Assembly of Zwitterionic Peptide Amphiphiles." J. Phys. Chem. B. vol. 108, No. 39, pp. 15278-15284.

Tsonchev, Stefan, Alessandro Troisi, George C. Schatz, and Mark A. Ratner. 2004. "On the Structure and Stability of Self-Assembled Zwitterionic Peptide Amphiphiles: A Theoretical Study." Nano Letters. vol. 4, No. 3, pp. 427-431.

Arnold, Michael S., Mustafa O. Guler, Mark C. Hersam, and Samuel I. Stupp. 2005. "Encapsulation of Carbon Nanotubes by Self-Assembling Peptide Amphiphiles." Langmuir. vol. 21, No. 10, pp. 4705-4709.

Behanna, Heather A., Jack J. J. M. Donners, Alex C. Gordon, and Samuel I. Stupp. 2005. "Coassembly of Amphiphiles with Opposite Peptide Polarities into Nanofibers." Journal of the American Chemical Society. vol. 127, No. 4, pp. 1193-1200.

Bitton, Ronit, Judith Schmidt, Markus Biesalski, Raymond Tu, Matthew Tirrell, and Havazelet Bianco-Peled. 2005. "Self-Assembly of Model DNA-Binding Peptide Amphiphiles." Langmuir. vol. 21, No. 25, pp. 11888-11895.

Bull, Steve R., Mustafa O. Guler, Rafael E. Bras, Palamadai N. Venkatasubramanian, Samuel I. Stupp, and Thomas J. Meade. 2005. "Magnetic Resonance Imaging of Self-Assembled Biomaterial Scaffolds." Bioconjugate Chem. vol. 16, No. 6, pp. 1343-1348.

de Loos, Maaike, Ben L. Feringa, and Jan H. van Esch. 2005. "Design and Application of Self-Assembled Low Molecular Weight Hydrogels." Eur. J. Org. Chem. pp. 3615-3631.

Guler, Mustafa O., Randal C. Claussen, and Samuel I. Stupp. 2005. "Encapsulation of Pyrene Within Self-Assembled Peptide Amphiphile Nanofibers." Journal of Materials Chemistry. vol. 15, pp. 4507-4512.

Guler, Mustafa O., Jonathan K. Pokorski, Daniel H. Appella, and Samuel I. Supp. 2005. "Enhanced Oligonucleotide Binding to Self-Assembled Nanofibers." Bioconjugate Chem. vol. 16, No. 3, pp. 501-503.

Jun, Ho-Wook, Virany Yuwono, Sergey E. Paramonov, and Jeffrey D. Hartgerink. 2005. "Enzyme-Mediated Degradation of Peptide-Amphiphile Nanofiber Networks." Adv. Mater. vol. 17, pp. 2612-2617.

Silva, Gabriel A. 2005. "Nanotechnology Approaches for the Regeneration and Neuroprotection of the Central Nervous System." Surgical Neurology. vol. 63, pp. 301-306.

Silva, Gabriel A. 2005. "Small Neuroscience: The Nanostructure of the Central Nervous System and Emerging Nanotechnology Applications." Current Nanoscience. vol. 1, No. 3, pp. 225-236.

Solis., F. J., S. I. Stupp, and M. Olvera de la Cruz. 2005. "Charge Induced Pattern Formation on Surfaces: Segregation in Cylindrical Micelles of Cationic-Anionic Peptide-Amphiphiles." The Journal of Chemical Physics. vol. 122, No. 5, 054905-1-054905-9.

Tovar, John D., Randal C. Claussen, and Samuel I. Stupp. 2005. "Probing the Interior of Peptide Amphiphile Supramolecular Aggregates." Journal of the American Chemical Society. vol. 127, No. 20, pp. 7337-7345.

Hosseinkhani, Hossein, Mohsen Hosseinkhani, and Hisatoshi Kobayashi. Jul. 2006. "Design of Tissue-Engineered Nanoscaffold Through Self-Assembly of Peptide Amphiphile." Journal of Bioactive and Compatible Polymers. vol. 21, No. 4, pp. 277-296.

Engler, Adam J., Shamik Sen, H. Lee Sweeney, and Dennis E. Discher. Aug. 25, 2006. "Matrix Elasticity Directs Stem Cell Lineage Specification." Cell. vol. 126, pp. 677-689.

Brunsveld, L., J. Kuhlmann, and H. Waldmann. 2006. "Synthesis of Palmitoylated Ras-Peptides and —Proteins." Methods. vol. 40, pp. 151-165.

Elgersma, Ronald C., Tania Meijneke, Remco de Jong, Arwin J. Brouwer, George Posthuma, Dirk T. S. Rijkers, and Rob M. J. Liskamp. 2006. "Synthesis and Structural Investigations of N-alkylated β-peptidosulfonamide-peptide Hybrids of the Amyloidogenic Amylin(20-29) Sequence: Implications of Supramolecular Folding for the Design of Peptide-Based Bionanomaterials." Organic & Biomolecular Chemistry. vol. 4, pp. 3587-3597.

Guler, Mustafa O., Lorraine Hsu, Stephen Soukasene, Daniel A. Harrington, James F. Hulvat, and Samuel I. Stupp. 2006. "Presentation of RGDS Epitopes on Self-Assembled Nanofibers of Branched Peptide Amphiphiles." Biomacromolecules. vol. 7, No. 6, pp. 1855-1863.

Harrington, Daniel A., Earl Y. Cheng, Mustafa O. Guler, Leslie K. Lee, Jena L. Donovan, Randal C. Claussen, and Samuel I. Stupp. 2006. "Branched Peptide-Amphiphiles as Self-Assembling Coatings for Tissue Engineering Scaffolds." Journal of Biomedical Materials Research Part A. pp. 157-167.

Hosseinkhani, Hossein, Mohsen Hosseinkhani, Ali Khademhosseini, Hisatoshi Kobayashi, and Yasuhiko Tabata. 2006. "Enhanced Angiogenesis Through Controlled Release of Basic Fibroblast Growth Factor from Peptide Amphiphile for Tissue Regeneration." Biomaterials. vol. 27, pp. 5836-5844.

Mardilovich, Anastasia, Jennifer A. Craig, Matthew Q. McCammon, Ashish Garg, and Efrosini Kokkoli. 2006. "Design of a Novel Fibronectin-Mimetic Peptide-Amphiphile for Functionalized Biomaterials." Langmuir. vol. 22, No. 7, pp. 3259-3264.

Paramonov, Sergey E., Ho-Wook Jun, and Jeffrey D. Hartgerink. 2006. "Self-Assembly of Peptide-Amphiphile Nanofibers: The Roles of Hydrogen Bonding and Amphiphilic Packing." Journal of the American Chemical Society. vol. 128, No. 22, pp. 7291-7298.

Rajangam, Kanya, Heather A. Behanna, Michael J. Hui, Xiaoqiang Han, James F. Hulvat, Jon W. Lomasney, and Samuel I. Stupp. 2006. "Heparin Binding Nanostructures to Promote Growth of Blood Vessels." Nano Letters. vol. 6, No. 9, pp. 2086-2090.

Reches, Meital and Ehud Gazit. 2006. "Molecular Self-Assembly of Peptide Nanostructures: Mechanism of Association and Potential Uses." Current Nanoscience. vol. 2, No. 2, pp. 105-111.

Stendahl, John C., Mukti S. Rao, Mustafa O. Guler, and Samuel I. Stupp. 2006. "Intermolecular Forces in the Self-Assembly of Peptide Amphiphile Nanofibers." Advanced Functional Materials. vol. 16, pp. 499-508.

Behanna, Heather A., Kanya Rajangam, and Samuel I. Stupp. 2007. "Modulation of Fluorescence Through Coassembly of Molecules in Organic Nanostructures." Journal of the American Chemical Society. vol. 129, No. 2, pp. 321-327.

Meijer, Joris T., Marjolijn Roeters, Valentina Viola, Dennis W. P. M. Löwik, Gert Vriend, and Jan C. M. van Hest. 2007. "Stabilization of Peptide Fibrils by Hydrophobic Interaction." Langmuir. vol. 23, No. 4, pp. 2058-2063.

Copping, Aaron M. and Vanda R. G. Pond. Dec. 9, 1950. "Folic Acid as a Growth-Factor for the Rat." Nature. No. 4232, p. 993.

Invitrogen. Printed Jan. 22, 2008. "Dulbecco's Modified Eagle Medium (D-MEM) (1X) Liquid (High Glucose)." http://www.invitrogen.com/content.cfm?pageID=95&fuseaction=MediaForm.dsp_mediaForm&productId.

Clemetson, K. J., and J. M. Clemetson. 1998. "Integrins and Cardiovascular Disease." CMLS Cellular and Molecular Life Sciences. vol. 54, pp. 502-513.

Dupin, Elisabeth, and Nicole M. Le Douarin. 2003. "Development of Melanocyte Precursors from the Vertebrate Neural Crest." Oncogene. vol. 22, pp. 3016-3023.

Mardilovich, Anastasia, and Efrosini Kokkoli. 2004. "Biomimetic Peptide—Amphiphiles for Functional Biomaterials: The Role of GRGDSP and PHSRN." Biomacromolecules. vol. 5, No. 3, pp. 950-957.

Cui, Honggang, Takahiro Muraoka, Andrew G. Cheetham, and Samuel I. Stupp. 2009. "Self-Assembly of Giant Peptide Nanobelts." Nano Letters. vol. 9, No. 3, pp. 945-951.

Niece, Krista L., Catherine Czeisler, Vibhu Sahni, Vicki Tysseling-Mattiace, Eugene T. Pashuck, John A. Kessler, and Samuel I. Stupp. 2008. "Modification of Gelation Kinetics in Bioactive Peptide Amphiphiles." Biomaterials. vol. 29, pp. 4501-4509.

Sampson, Wayne R., Heather Patsiouras, and Nicholas J. Ede. 1999. "The Synthesis of 'Difficult' Peptides Using 2-Hydroxy-4-Methoxybenzyl or Pseudoproline Amino Acid Building Blocks: a Comparative Study." Journal of Peptide Science. vol. 5, pp. 403-409.

Jun, Ho-Wook, Virany Yuwono, Sergey E. Paramonov, and Jeffrey D. Hartgerink. 2005. "Enzyme-Mediated Degradation of Peptide-Amphiphile Nanofiber Networks." Advanced Materials. vol. 17, pp. 2612-2617.

Kirkham, J., A. Firth, D. Vernals, N. Boden, C. Robinson, R. C. Shore, S. J. Brookes, and A. Aggeli. 2007. "Self-Assembling Peptide Scaffolds Promote Enamel Remineralization." J. Dent. Res. vol. 86, No. 5, pp. 426-430.

Stryker, Lori. 2008. "Titanium Dioxide: Toxic or Safe?" The Organic Make-up Company Inc. www.organicmakeup.ca/ca/titaniumdioxide.asp. 4 pages. Printed Aug. 25, 2010.

* cited by examiner

Figure 3A      Figure 3B
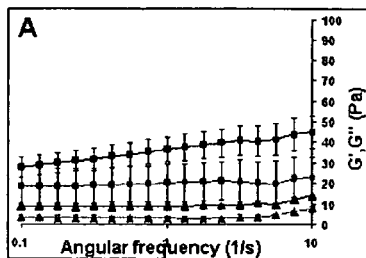 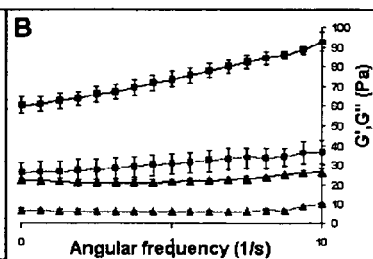
Figure 3C 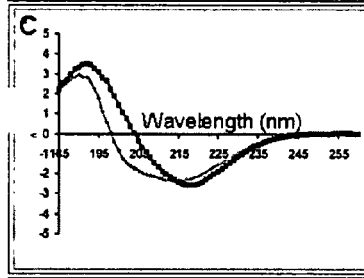 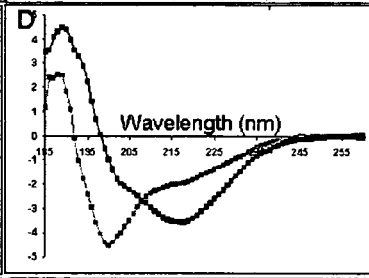 Figure 3D
Figure 3E 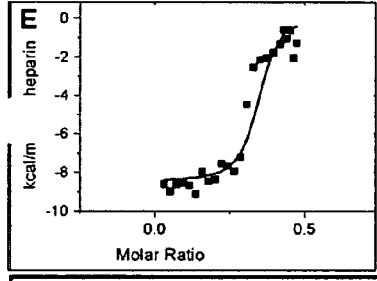 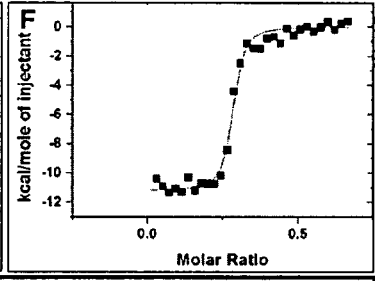 Figure 3F
| G | HBPA-1-Heparin | HBPA-2-heparin |
|---|---|---|
| ΔG | -9616.74+/-29.18 | -10164.948+/-233.49 |
| ΔH | -6.24+/-0.01 | -9218.5+/-3864.06 |
| -TΔS | -9610.5+/-29.20 | -946.448+/-3630.57 |
Figure 3G Figure 4
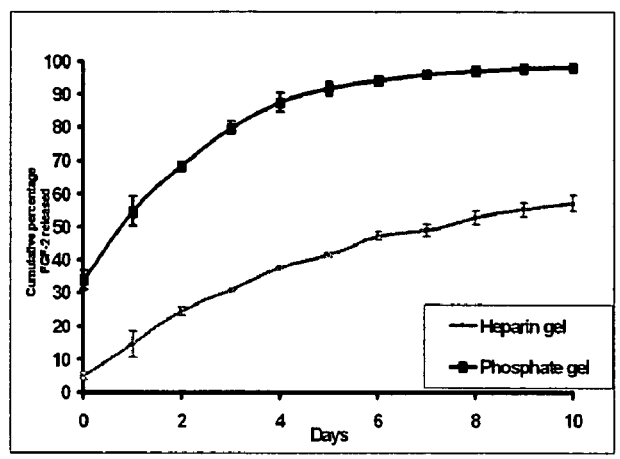
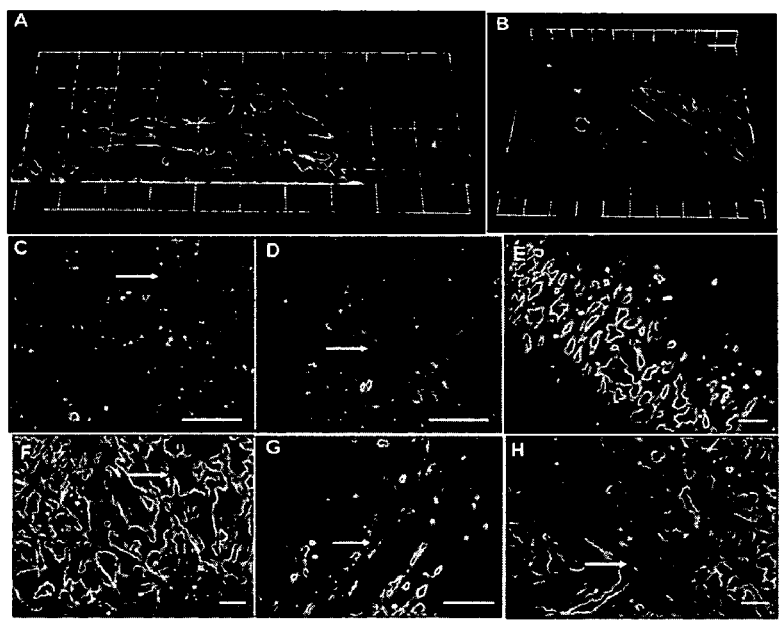
Figure 5A-H

ANGIOGENIC HEPARIN-BINDING EPITOPES, PEPTIDE AMPHIPHILES, SELF-ASSEMBLED COMPOSITIONS AND RELATED METHODS OF USE

This application claims priority benefit from provisional application Ser. No. 60/658,503, filed Mar. 4, 2005, the entirety of which is incorporated herein by reference.

This invention was made with government support under Grant No. R01 EB003806-01 awarded by the National Institutes of Health and Grant Number W81XWH-05-1-0381 awarded by the U.S. Army Medical Research and Material Command. The U.S. government has certain rights in the invention.

BACKGROUND OF THE INVENTION

Angiogenesis, the process of forming new blood vessels from existing ones, is essential for normal wound healing, and is well regulated by the body. Inadequate angiogenesis can give rise to a variety of disease conditions, including chronic skin wounds and myocardial infarction. Angiogenesis will increasingly become important for tissue engineering because implanted scaffolds, whether they deliver autologous cells or recruit host cell infiltration, need to have a blood supply to support the formation of living tissue. Toward this goal, a concern has been the development of a biocompatible matrix that can actively promote angiogenesis, with designed chemical and structural versatility, such that with appropriate modifications it could be used as a vascularizing scaffold to promote both tissue healing and tissue growth. Further, such a matrix would also be useful in promoting ischemic wound healing as seen after myocardial infarction and in chronic skin wounds. The development of and implementation of such systems have been on-going concerns in the art. However, various approaches previously taken suggest the need for continued improvement and provide the impetus toward further effort and innovation.

BRIEF DESCRIPTION OF THE DRAWINGS

FIGS. 3A-G. HBPA-1 and 2 interactions with heparin. 3A and 3B show oscillating rheometry of heparin and base triggered HBPA-1 gels (3A) and HBPA-2 gels (3B). The black curves in both figures are of heparin triggered gels and the grey curves are of base triggered gels with squares representing the elastic modulii and triangles the viscous modulii. The elastic modulii of all the gels are statistically higher than the viscous modulii and further the heparin triggered gels in both cases are statistically higher than that of the base triggered gels ($p<0.05$, values represent average and standard deviation). 3C and 3D show circular dichroism spectra of HBPA-1 solution (3C) and HBPA-2 solution (3D) revealing a predominant α helical conformation (grey), changing to predominantly β sheet conformation (black) after heparin is added in both cases. 3E and 3F show the integrated values of the heat change (black dots) and the fit line (line) obtained upon addition of increments of heparin into a solution of HBPA-1 (3E) and HBPA-2 (3F) plotted against the molar ratio of heparin to the HBPAs in order to obtain the respective $K_a$. Table 3G compares the thermodynamic signature of HBPA-1 and HBPA-2 interaction with heparin. While the ΔG in both cases is similar, ΔH is predominant in SPA heparin interaction indicating an entropically driven reaction while −TΔS is predominant in HBPA heparin interaction indicating an enthalpically driven reaction.

FIG. 4. Slow release of rhodamine-FGF-2 from a network of HBPA-1-heparin gel (gray curve) vs. the more rapid release from a HBPA-1-Na$_2$HPO$_4$ gel (black curve)(Bars are standard deviations).

FIGS. 5A-H. In vitro angiogenesis assay. Fluorescent confocal micrographs of bPAECs stained with Vybrant CFDA in heparin-nucleated HBPA-1 gels with (A) and without the growth factors (B). The black channels are continuous lumina extending in three dimensions (each side of scale grid in (A) is 75 μm and in (B) is 37 μm). Samples corresponding to HBPA-2-heparin gels with (C) and without (D) growth factors (scale bars=80 μm) shows occasional slit like lumen (arrows). Collagen control gels, with growth factors incorporated within the collagen gel (E) shows cells growing with no particular orientation; whereas collagen gels with supplemental heparin (F), with supplemental growth factors (G) and both supplemental heparin and growth factors (H), all show anastomosing networks with occasional slit-like lumina (arrows) (scale bar for C-F=40 μm).

SUMMARY OF THE INVENTION

Figure 1:
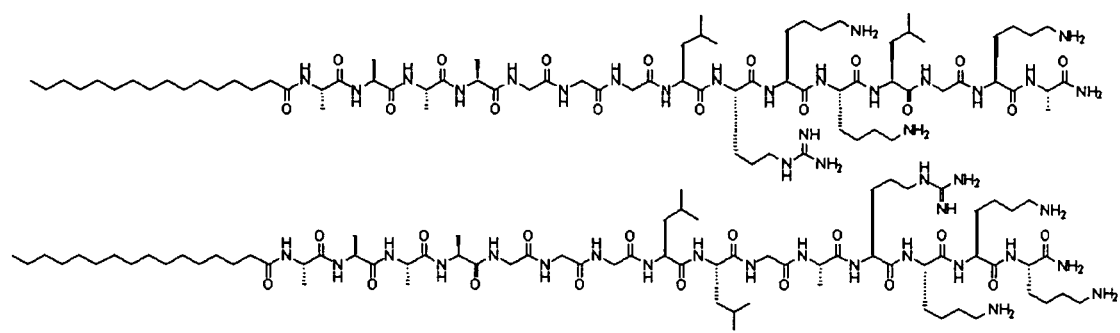
FIG. 1. Structures of HBPA-1 (top) and HBPA-2 (bottom) amphiphilic peptide compounds, in accordance with certain embodiments of this invention.

In light of the foregoing, it is an object of the present invention to provide a range of amphiphilic peptide compounds, related heparin-bound compositions and/or their use in one or more angiogenic methods, thereby overcoming various deficiencies and shortcomings of the prior art, including those outlined above. It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It can be an object of the present invention to provide a range of structurally diverse amphiphilic peptide compounds interactive with one or more sulfated glycosaminoglycan components, such interaction favorably compared with the prior art with respect to the affinity of such components toward angiogenic growth factors.

It can be another object of the present invention, in conjunction with one or more of the aforementioned compositions, to provide for the activation, binding, delivery and/or release of one or more angiogenic growth factors.

It can be another object of the present invention to provide one or more methods, and compositions useful in conjunction therewith, of inducing angiogenesis, to promote tissue healing and/or growth.

Other objects, features, benefits and advantages of the present invention will be apparent from this summary and the following descriptions of certain embodiments, and will be readily apparent to those skilled in the art having knowledge of various peptide amphiphiles, sulfated polysaccharide bound compositions and/or their use in the promotion of angiogenesis. Such objects, features, benefits and advantages will be apparent from the above as taken into conjunction with the accompanying examples, data, figures and all reasonable inferences to be drawn therefrom, alone or with consideration of the references incorporated herein.

In part, the present invention can be directed to an amphiphilic peptide compound comprising a hydrophobic component and a peptide component. The hydrophobic component can be coupled to the peptide component at, near or about either the C-terminus or the N-terminus of the peptide component. The peptide component can comprise at least one residue capable of non-covalent interaction or binding with a sulfated polysaccharide. Without limitation, such residues can be interactive with or have a non-covalent binding affinity for a sulfated glycosaminoglycan component including but not limited to heparin sulfate, heparan sulfate and combinations thereof. As illustrated elsewhere herein and described more fully in one or more of the references incorporated hereinafter, the hydrophobic component of such a compound can comprise such a moiety ranging from about $C_4$ or about $C_6$ to about $C_{22}$ or higher.

Regardless, interactive residues can comprise at least one hydrophobic residue, as can be designated X, such a residue as can be selected from alanine, glycine, leucine, isoleucine, phenylalanine, proline, valine and combinations thereof. Likewise, without limitation as to identity of residue(s) X, the peptide component can comprise at least one basic residue, as can be designated B, including but not limited to arginine, histidine and lysine. In certain embodiments, the interactive residues can comprise a sequence selected from but not limited to XBBBXXBX, XXXXBBBB, XXXXBBB, XXXXBB, and XXXXB, wherein X and B can be independently selected from any of the aforementioned hydrophobic and basic residues, respectively. For instance, the peptide components of such compounds can comprise residues comprising a sequence selected from SEQ ID NO:1 LRKKLGKA and SEQ ID NO:2 LLGARKKK. Regardless, the peptide component can also comprise one or more bioactive epitope sequences of the sort described below or discussed more fully in one or more of the incorporated references. In certain other embodiments, with or without such a bioactive epitope and without limitation as to interactive residue sequence, the C-terminus of the peptide component can comprise either an amide or a carboxyl moiety.

In part, this invention can also be directed to a composition comprising a sulfated polysaccharide and one or more amphiphilic peptide compounds of the sort described above. Non-covalent interaction of such a sulfated polysaccharide component with an amphiphilic peptide compound can, in an appropriate medium, induce a micellar configuration. For instance, a hydrogel of one or more of the aforementioned peptide components can be induced, in an aqueous medium, by contact with or incorporation of a sulfated glycosaminoglycan. In certain other embodiments, as illustrated below, such compositions can also comprise an angiogenic growth factor. Such growth factors include those as would be understood known or determined by those skilled in the art, representative non-limiting examples of which can be selected from those currently known, and as may later be determined to be, heparin binding or heparan binding growth factors, including but not limited to those designated VEGF and FGF-2, and combinations thereof.

In part, the present invention can also be directed to a method of inducing angiogenesis. Such a method can comprise, without limitation as to order or progression, providing one or more amphiphilic peptide compounds of the sort described above; incorporating therewith a sulfated glycosaminoglycan; and contacting the resulting composition with a cellular medium and/or an angiogenic growth factor. Contact with a cellular medium can be for a time and in an amount of the composition and/or growth factor at least partially sufficient for angiogenesis.

The peptide component of such an amphiphilic compound or a resulting composition can comprise residues comprising a sequence selected from XBBBXXBX, XXXXBBBB, XXXXBBB, XXXXBB, and XXXXB, wherein X can be independently selected from alanine, glycine, leucine, isoleucine, phenylalanine, proline and valine. Likewise, without limitation as to the identity of residue(s) X, residue B can be independently selected from arginine, histidine and lysine. Regardless of sequence, such residues can be interactive with any one or more of the range of known sulfated glycosaminoglycan components, such as but not limited to heparin sulfate, heparan sulfate and combinations thereof. As illustrated elsewhere herein, incorporation of such a glycosaminoglycan component can be used to induce gelation of the peptide compound(s), to provide the resulting composition a micellar configuration. Accordingly, such incorporation and resulting gelation can be effected prior to contact with a cellular medium. In the alternative, an amphiphilic peptide compound can be introduced to or contacted with a cellular medium. Thereafter, incorporation of a glycosaminoglycan component can induce in situ gelation—at, on or within the cellular medium.

In part, this invention can also be directed to a method of using an amphiphilic peptide composition to activate an angiogenic growth factor. Such a method can comprise providing an amphiphilic peptide-sulfated polysaccharide composition of the sort described above; and interacting such a composition with an angiogenic growth factor, as illustrated elsewhere herein to induce angiogenesis in vitro, in vivo, or as would otherwise be recognized by those skilled in the art as indicative of the activation of such growth factors.

In certain embodiments, such interaction can comprise introduction of one or more growth factors to such a composition, either before or after contact between the composition and cellular medium. In certain other in vivo embodiments of such a methodology, interaction can be substantially absent exogenous growth factor, with respect to the cellular medium. As illustrated below, representative of such embodiments, in vivo angiogenesis can be observed, without introduction or addition of an angiogenic growth factor, after cellular contact. Accordingly, various embodiments of this methodology can be used to activate an angiogenic growth factor, induce or promote angiogenesis and treat mammalian ischemic tissue.

DETAILED DESCRIPTION OF CERTAIN EMBODIMENTS

Illustrating certain embodiments of this invention, one or more peptide amphiphile (PA) compounds can be used as a chemical platform to produce a self-assembling, angiogenic scaffold. Such peptide amphiphiles can comprise a hydrophilic peptide head group and a hydrophobic fatty acid tail to induce self-assembly into nanofibers in aqueous solution. For instance, as can be applicable to certain embodiments, a gel or a hydrogel network can be created through utilization of appropriate changes in pH or ionic strength. See, Hartgerink, J. D., E. Beniash and S. I. Stupp; "Self-assembly and mineralization of peptide-amphiphile nanofibers." *Science* 294, (2001) 1684-1688, incorporated herein by reference in its entirety.

Alteration of the peptide sequence can be used to impart distinct biological functionalities to the resulting nanofibers. For instance, a peptide amphiphile with a heparin-binding head group can be used because heparin, part of a group of related glycosaminoglycans called heparan sulfate like glycosaminoglycans (HSPGs) that are normally found in the extracellular matrix, are believed to play a role in angiogenesis. HSPGs comprise sulfated glycosaminoglycans including heparin sulfate and its close structural analog heparan sulfate. HSPGs bind to and activate many angiogenic growth factors, in particular-vascular endothelial growth factor (VEGF) and fibroblast growth factor-2 (FGF-2). See, e.g., the following, each of which is incorporated herein in its entirety, Keyt, B. A., L. T. Berleau, H. V. Nguyen, H. Chen, H. Heinsohn, R. Vandlen and N. Ferrara; "The carboxyl-terminal domain (111-165) of vascular endothelial growth factor is critical for its mitogenic potency." *Journal of Biological Chemistry* 271, (1996) 7788-7795. Herr, A. B., D. M. Ornitz, R. Sasisekharan, G. Venkataraman and G. Waksman; "Heparin-induced self-association of fibroblast growth factor-alpha-evidence for two oligomerization processes." *Journal of Biological Chemistry* 272, (1997) 16382-16389. Schlessinger, J., A. N. Plotnikov, O. A. Ibrahimi, A. V. Eliseenkova, B. K. Yeh, A. Yayon, R. J. Linhardt and M. Mohammadi; "Crystal structure of a ternary fgf-fgfr-heparin complex reveals a dual role for heparin in fgfr binding and dimerization." *Molecular Cell* 6, (2000) 743-750. This approach imparts versatility to the resulting matrices, as HSPGs are capable of binding and activating many organogenic growth factors across different systems. Various other sulfated polysaccharides can be considered in conjunction with the design of useful peptide sequences. For instance, consistent herewith, residues interactive with carrageenan are incorporated within a peptide component.

Another level of versatility is provided by the peptide amphiphile, itself, since a wide range of peptide epitopes can be incorporated on the periphery of the nanofibers, and judicious design of the molecules can enable co-assembly of multiple PAs with different epitopes into hydrogels. (Niece, K. L., J. D. Hartgerink, J. Donners and S. I. Stupp; "Self-assembly combining two bioactive peptide-amphiphile molecules into nanofibers by electrostatic attraction." *Journal of the American Chemical Society* 125, (2003) 7146-7147, incorporated herein by reference in its entirety.)

In conjunction with the preceding, unique heparin binding sequences can be synthesized, including but not limited to —XBBBXXBX—, where X can be independently selected from hydrophobic amino acid residues and B can be independently selected from basic amino acid residues. The most commonly occurring amino acids in this motif can be determined from a group of naturally occurring heparin-binding proteins. (Cardin, A. D. and H. J. R. Weintraub; "Molecular modeling of protein-glycosaminoglycan interactions." *Arteriosclerosis* 9, (1989) 21-32.) A heparin binding peptide amphiphile (HBPA) of this invention is shown here to self-assemble with the addition of heparin or heparan, leading to formation of a gel. Further, a resulting compositional matrix has the capability to induce endothelial cells sandwiched within it to form highly organized, capillary-like structures with continuous lumen in three dimension; and, a resulting matrix with heparan has been shown to significantly improve ischemic wound healing even without growth factors—something not observed in the literature with any other type of matrix.

In one respect, compounds of this invention can comprise a peptide amphiphile incorporating such a binding sequence; that is, any heparin-binding peptide amphiphile of the form:

(hydrophobe)—(spacer)—XBBBXXBX—(terminus)

where the hydrophobe component is any saturated or unsaturated alkane or other hydrophobic moiety, (spacer) is an optional component comprising an arbitrary amino acid sequence, X can be independently selected from alanine, glycine, leucine, isoleucine, phenylalanine, proline and valine, and B can be independently selected from arginine, histidine, and lysine and (terminus) is an amide or carboxyl terminated amino acid residue or sequence or other epitope which may be known or determined to be bioactive, such as but not limited to RGD, IKVAV (SEQ ID NO: 5), and biotin. Various other epitopes are known in the art and/or as described in one or more of the incorporated references.

Without limitation, one of the HBPA compounds of this invention can comprise a fatty acid, e.g. a palmitic acid, moiety or otherwise hydrophobic component covalently linked or coupled to a peptide sequence such as SEQ ID NO:3 AAAAGGGLRKKLGKA, with a terminal alanine residue optionally amide terminated. The presence of a hydrophobe induces self-assembly into nanofibers in aqueous solutions when triggered with appropriate stimuli, such as the addition of heparin. Further, appropriate concentrations of the HBPA with the addition of heparin, heparan or similar highly charged polymers causes the formation of a self-supporting hydrogel, due to the entanglement of bundles of nanofibers. This HBPA-heparin interaction is non-covalent, which is an improvement over current covalently bound heparin matrices as non-covalent interaction simulates biological interaction of heparin to extra-cellular matrix. The non-covalent interaction also allows the heparin to bind and activate angiogenic heparin-binding growth factors, such as vascular endothelial growth factor (VEGF) and fibroblast growth factor (FGF-2), and control their release from the matrix.

In particular, certain embodiments of this invention can comprise a heparin-binding peptide comprising the amino acid sequence, SEQ ID NO:1—LRKKLGKA—which is both novel and potentially useful for covalent or non-covalent attachment to a wide range of bioactive polymers, scaffolds and tissue or cell culture substrates where binding of heparin or heparin-like polymers is desired. Further, since the bulk of the non-covalent interaction between heparin and the heparin binding peptide amphiphile can be explained at least in part by electrostatic attraction, other, related sequences have also been prepared in the form of peptide amphiphiles, following the general format of (hydrophobe)—(spacer)—XXXX-BBBB—(terminus); (hydrophobes)—(spacer)—XXXX-BBB—(terminus); (hydrophobe)—(spacer)—XXXXBB—(terminus) and (hydrophobe)—(spacer)—XXXXB—(terminus) where the hydrophobe component, the optional (spacer) component, X, B and (terminus) are as defined above.

Specifically, one such peptide amphiphile includes but is not limited to the structure: palmitoyl—SEQ ID NO:4 AAAAGGGLLGARKKK with an amide terminus. Regardless, the peptide component of amphiphilic compounds useful with this invention is limited only by capacity to bind and/or utilize heparin, and/or functionally equivalent heparin derivatives or analogs thereof, according to or consistent with the descriptions herein or as would be inferred by those skilled in the art made aware of this invention.

Regardless of heparin-binding capability, the peptide amphiphiles of this invention can comprise a peptide component of varied length or sequence depending upon desired flexibility, charge and/or capacity for intermolecular interaction or binding enroute to nanofiber formation. A hydrophobic component of such compounds can also be varied (e.g., moieties ranging from about $C_4$ or about $C_6$ to greater than about $C_{22}$ or higher alkyl or substituted alkyl, saturated or unsaturated, etc.), such components limited only by resulting amphiphilic character and effect on compositions or assemblies of such compounds.

Various peptide amphiphile compounds used in conjunction with the present invention, with consideration of any one or more of the preceding considerations, can be synthesized using preparatory techniques well-known to those skilled in the art, including those disclosed in co-pending application Ser. Nos. 10/294,114 filed Nov. 14, 2002 (International Publication No. WO 03/054146) and 10/368,517 filed Feb. 18, 2003 (International Publication No. WO 03/070749), each of which are incorporated herein by reference in their entirety, and modifications of those techniques known in the literature and as referenced elsewhere herein. The synthetic schemes set forth in such references and co-pending applications may be applied to the present invention. Peptide amphiphiles may be fully protonated, partially protonated, or as acid or basic addition salts. Generally, such peptide amphiphiles can be prepared using standard solid-phase peptide chemistry including addition of a hydrophobic tail or component at or near the N-terminus of the peptide component. Modifications of such synthetic techniques can be made as would be known to those skilled in the art and aware of this invention, such as by using procedures and the corresponding peptide amphiphile moieties, compounds, related compositions, and configuration or assemblies described in co-pending application Ser. Nos. 11/005,314 and 11/005,552 filed on Dec. 6, 2004 (International Publication Nos. WO 05/056576 and WO 05/056039, respectively), each of which is incorporated herein by reference in its entirety.

Figures 2A, 2B, 2C:
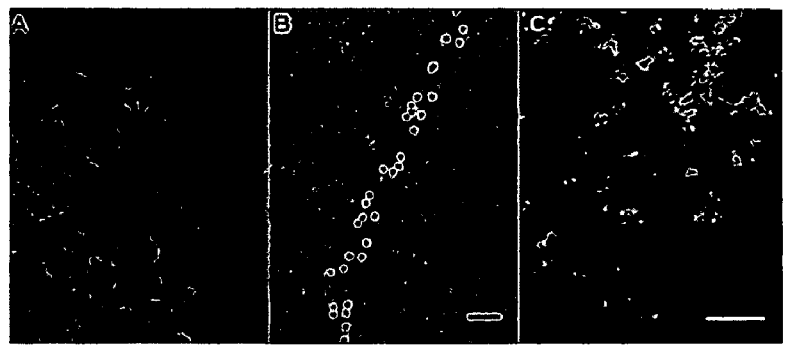
FIGS. 2A-C. Transmission electron micrographs of heparin triggered bundles of nanofibers of HBPA-2 (2A, scale bar 50 nm) and HBPA-1 (2B, scale bar 40 nm). 2B also shows heparin tagged to gold nanoparticles (black dots) decorating the nanofibers. 2C shows confocal fluorescent micrograph of fluorescein heparin staining bundles of HBPA-1 fibers (scale bar 100 μm).

An HBPA compound can comprise, for example, a fatty acid tail derived from palmitic acid, a linker peptide of four alanines and three glycines and a novel heparin binding peptide head group containing the amide terminated sequence SEQ ID NO:1 LRKKLGKA (referred to as HBPA-1 henceforth) or the amide terminated sequence SEQ ID NO:2 LLGARKKK (referred to as HBPA-2 henceforth) (see FIG. 1). Both HBPA-1 and -2 are readily soluble in water, and self-assemble to form bundles of nanofibers in solution. At concentrations above six millimolar of the two HBPAs, addition of heparin or heparan triggered gel formation. These bundles of nanofibers were visualized by transmission electron microscopy (TEM) shown in FIG. 2A, with heparin tagged gold particles seen decorating HBPA-1 nanofibers (FIG. 2B). Further, fluorescent confocal microscopy showed bundles of HBPA-1 fibers to be stained by heparin tagged to fluorescein, as shown in FIG. 2C. Frequency sweep oscillating rheology revealed viscoelastic gel-like behavior for these materials, with both the storage (G') and loss (G") modulus largely independent of the angular frequency and G' consistently higher than G" (see FIGS. 3A and 3B). The HBPAs also gelled both at elevated pH (base triggered) and with the addition of disodium hydrogen phosphate. Further, the elastic modulii of the heparin triggered gels was statistically higher in both cases as compared to the respective base triggered gels indicating increased stiffness (FIGS. 3A and 3B).

Circular dichroism (CD) spectroscopy of HBPAs showed a CD signature with predominant alpha helical content. This changed with the addition of heparin into a signature suggestive of beta sheet formation with typical negative and positive maxima at 218 nm and 192 nm respectively (see FIGS. 3C and 3D). Isothermal titration calorimetry was used to titrate increments of heparin independently into both the HBPAs and measured the heat released upon binding as a function of the molar ratio. The data obtained was integrated and fitted to a nonlinear function as previously described (Fromm, J. R., et al, "Differences in the Interaction of Heparin with Arginine and Lysine and the Importance of These Basic-Amino-Acids in the Binding of Heparin to Acidic Fibroblast Growth-Factor" Arch. Biochem. Biophys. 323 (1997) 279) to obtain an association constant of $10^7$ in both cases (see FIGS. 3E and 3F). Despite similarity in their binding constants, the binding interaction of HBPA-1 and HBPA-2 were energetically very different. The HBPA-1 and heparin interaction appears to have been predominantly driven by entropic changes whereas the HBPA-2-heparin interaction was predominantly enthalpic (Table 3G). Such results can be explained with reference to their respective structures. HBPA-1 has hydrophobic residues on the periphery of its peptide chain and the increase in entropy is possibly due to displacement of solvent water molecules from these residues upon heparin interaction. HBPA-2, on the other hand, has the charged basic residues on the periphery leading to strong electrostatic forces with the negatively charged heparin, and hence the predominance of enthalpic factors in their interaction.

A release profile of fibroblast growth factor-2 (FGF-2) from HBPA-1-heparin gel was determined, illustrating another aspect of this invention. FGF-2 covalently linked to rhodamine (ex/em maxima at 544/576 nm) was incorporated into HBPA-1 hydrogels prepared with either the addition of heparin or disodium hydrogen phosphate. The release media was exchanged and stored at a series of time points. The passive cumulative release profiles of the FGF-2 rhodamine revealed that, in the absence of heparin, 34.1% of the FGF-2 was released from the gel within the first five minutes and 98.3% was released by day 10. The presence of heparin reduced the rate and the absolute release of the FGF-2 to a total of 57.1% by day 10 (see FIG. 4).

To demonstrate in vitro angiogenesis, bovine pulmonary artery endothelial cells (bPAEC) were grown to confluence on top of a layer of both types of HBPA-heparin gel and then sandwiched by the application of another layer of the same gel in an 8-well chambered coverslip. Some gels had a combination of VEGF and FGF-2 incorporated within them. Four controls were used: bPAECs sandwiched within two layers of type I collagen gels to which no supplemental heparin or growth factors were added; supplemental heparin alone; growth factors alone; or both heparin and growth factors added at each media change. The bPAECs grew in sheets and showed branched anastomosing networks as early as one day after the addition of the second layer in the HBPA-1-heparin gels with growth factors. This organization continued and by day 7 showed formation of organized tubular structures with continuous lumens penetrating through the thickness of the gel (see FIG. 5A). The HBPA-1-heparin gels without growth factor started showing some branching later at day 3. At day 7, these gels appeared to have fewer tubules than the ones seen in the HBPA-1-heparin gels with growth factors, but the individual tubules in both types of gels showed remarkable similarity (FIG. 5B). In the case of the HBPA-2 heparin gels, the cells grew in sheets in three dimensions with occasional slit like lumens and rare tubular structures seen at the end of ten days in gels with and without growth factors (FIGS. 5C and D). The collagen gels with no supplemental heparin or growth factors showed the presence of bPAECs growing throughout the gels with no particular organization. The three types of gels with supplemental heparin, growth factors or both showed the presence of branched anastomosing networks in some of the areas. None showed the formation of organized tubular structures with continuous lumen (FIGS. 5E-H).

Finally, in order to demonstrate the functional efficacy of such a composition and matrix configuration in vivo, a rabbit ear wound healing model was chosen. (See, e.g., Ahn S T, Mustoe T A. "Effects of ischemia on ulcer wound healing: a new model in the rabbit ear." *Ann Plast Surg.* 24 (1990) 17-23, the entirety of which is incorporated herein by reference.) This is a well-established model wherein ischemia is induced surgically by tying off two of the three arteries which supply the normal rabbit ear and interrupting skin circulation circumferentially at the ear base. Then, four wounds are created on the ventral aspect of the ear using a circular 6 mm biopsy punch upto and including the perichondrium. The desired materials in this case HBPA-1 heparan gel with and without the growth factors (VEGF and FGF-2) as the case may be are applied and the wound is covered with a polyurethane film dressing and followed up for twelve days. At the end of twelve days, the animals are euthanized and the wounds are harvested using a through and through 7 mm biopsy around the wound. The samples are analyzed for histological evidence of wound healing. This healing process can be quantified by measuring the epithelial gap between the healing edges in a bisected wound. Four control materials were also used namely HBPA-1 with growth factors, heparan with growth factors, growth factors alone and a buffer solution alone (the solvent for the above materials).

Figure 6:
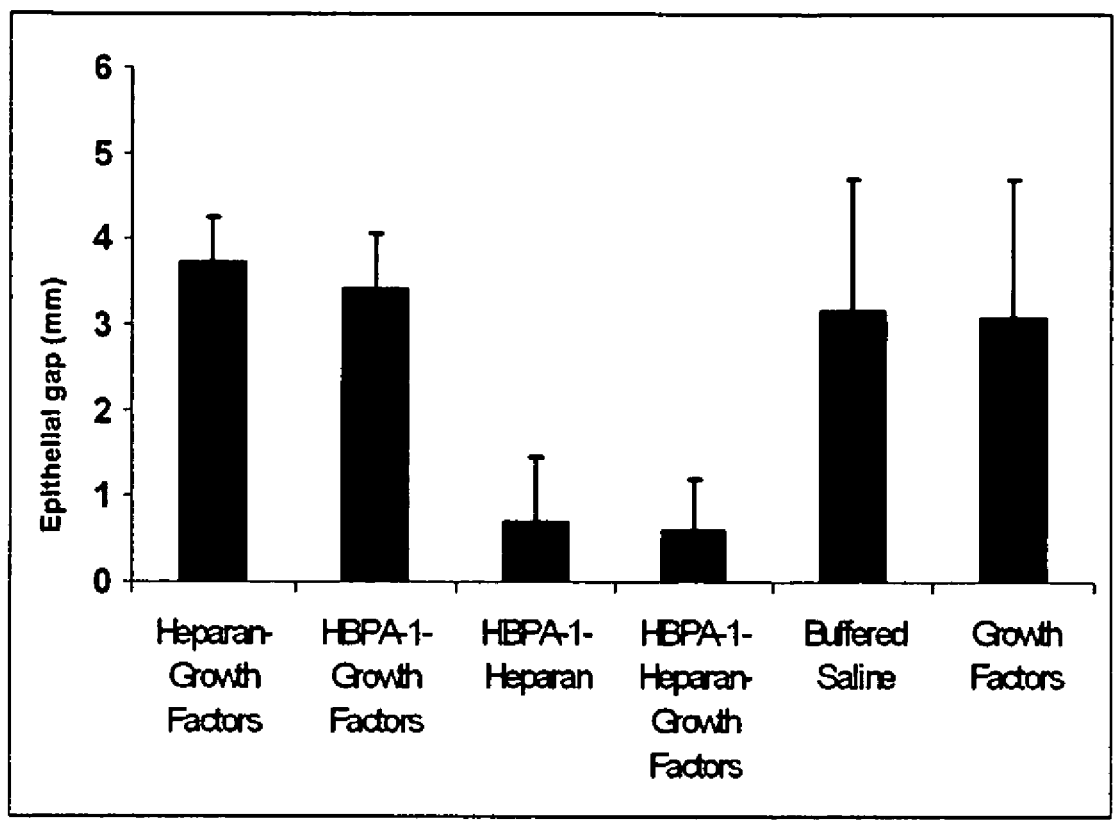
FIG. 6 In vivo ischemic wound healing assay. The epithelial gap measured twelve days after creation of a 6 mm wound on an ischemic rabbit ear. HBPA-1-heparan gels with and without growth factors induced statistically significant wound healing as compared to all other controls ($p<0.05$, graph represents average and 95% confidence levels).

Analyzing the wound edge results, it was found that the HBPA-1-heparan gels induced statistically significantly higher wound healing than any of the controls. The presence of exagenous or introduced growth factors did not seem to be necessary to affect the ability of the matrix to induce wound healing (see FIG. 6). Induced wound healing in ischemic wounds without the use of growth factors has not been previously reported. Without limitation to any one theory or mode of operation such observations may be due to the ability of the heparan in the composition and resulting matrix configuration to recruit and activate endogenous growth factors found locally within the cellular medium.

Heparin and heparan are important promoters of angiogenesis due to their ability to bind and activate angiogenic growth factors. Other studies have used heparin to release angiogenic growth factors by covalently binding it to a matrix, physically trapping it within a matrix or by coating the surface of a matrix with heparin. In contrast to the art, this invention incorporated heparin and or heparan non-covalently, using a consensus heparin-binding sequence on a peptide amphiphile (HBPA), to form a hydrogel with the potential to recruit, activate and/or deliver growth factors to cells in a way that mimics the function of heparin in the extracellular matrix.

The self-assembly of other peptide amphiphile molecules into nanofibers that entangle to form gels has been previously described. See, e.g., Hartgerink, J. D., E. Beniash and S. I. Stupp; "Peptide-amphiphile nanofibers: A versatile scaffold for the preparation of self-assembling materials." *Proceedings of the National Academy of Sciences of the United States of America* 99, (2002) 5133-5138. Briefly, it is believed, without limitation to any one theory or mode of operation, that when the pH of the solution is acidic, the HBPAs have a net positive charge that inhibits self-assembly through electrostatically repulsion. As the pH of the solution is raised, the positive charges are neutralized, facilitating aggregation through hydrophobic collapse and the formation of a hydrogen-bonded peptide secondary structure. Gel formation occurs due to entanglement of nanofibers and requires an appropriate concentration of the HBPA. Simple inorganic counter ions have also been shown to promote this self-assembly and gel formation, presumably due to a similar charge-shielding role. Here, self-assembly is observed either with addition of inorganic anions from $Na_2HPO_4$ or with complex polymeric anions—the glycosaminoglycans, heparin sulfate and heparan sulfate. Heparin-triggered self-assembly and gel formation is interesting, as (1) it is the first described instance of a polymeric substance triggering supramolecular self-assembly, and (2) because the peptide component was specifically designed to bind to such glycosaminoglycans. Heparin can be considered as not only performing a simple charge shielding role, but as also involved in forming noncovalent crosslinks between nanofibers. As such, heparin could bind to multiple HBPA molecules, of differing hydrophobic components or residue sequences, and thus template a mixed supramolecular self-assembly.

The interactions of the HBPAs with the heparin are further confirmed by CD spectroscopy and isothermal calorimetry. The binding constant obtained by ITC of 100 nM is indicative of strong binding and is comparable to that obtained between other synthetic heparin binding peptides and heparin. At the same time, this is two orders of magnitude weaker than the binding constant of heparin to a heparin binding growth factor like FGF-2, and hence heparin containing hydrogels are able to retain FGF-2 for longer periods of time than the HBPA alone and slow its release from the hydrogel.

The cell sandwich in-vitro assays showed the presence of highly organized, tubular structures with continuous lumen penetrating through the thickness of the HBPA-1-heparin gels. The structures seen closely resembled in vivo capillary networks with a degree of organization not previously reported. This behavior was seen only in the HBPA-1-heparin gels. The HBPA-1-heparin gels with growth factors were observed to organize sooner and over larger areas than the gels without growth factors. Though the presence of added growth factors induced earlier anastomosis, the gels without growth factors also exhibit similar organization, possibly due to the ability of the noncovalently bound heparin in the gel to recruit and activate growth factors from the serum and those synthesized by the cells themselves. This would explain the qualitative similarity of the tubular processes in the HBPA-1-heparin gels both with and without growth factors and the delay in organization of the cells in the HBPA-1-heparin gels without growth factors. It can be postulated that formation of bundles of nanofibers non-covalently exhibiting heparin on its surface optimizes the bioactivity of heparin for this particular application. In contrast, the HBPA-2 heparin gels show occasional discontinuous slit-like lumen similar to the control collagen gels. This could be because the presence of the consensus format in the first case optimizes this particular bioactivity of heparin. Consensus heparin-binding sequences of naturally occurring heparin-binding proteins are thought to form a positively charged alpha turn of 20 A around the negatively charged repeat unit of heparin. (Margalit, H., N. Fischer and S. A. Bensasson; "Comparative-analysis of structurally defined heparin-binding sequences reveals a distinct spatial-distribution of basic residues." *Journal of Biological Chemistry* 268, (1993) 19228-19231.)

Finally, in vivo models of ischemic wound healing on rabbit ears shows that HBPA-1 heparan gels even without growth factors significantly induces wound healing which would result from improved angiogenesis locally. Of striking note is the fact that this wound healing was accomplished even without the angiogenic growth factors. This is probably due to the presence of endogenous growth factors at the wound site which is being recruited and activated by the HBPA-1 heparan matrix. This is a completely novel result and in fact previous studies have shown a partial improvement with wound healing in this model only with the use of micrograms of growth factors (Corral C J, Siddiqui A, Wu L, Farrell C L, Lyons D, Mustoe T A. "Vascular endothelial growth factor is more important than basic fibroblastic growth factor during ischemic wound healing." *Arch Surg.* 134 (1999), 200-205).

Accordingly, the present invention can provide a novel class of peptide amphiphile biomolecules that self-assemble and bind noncovalently to heparin, heparan, and other sulfated glycosaminoglycans, giving rise to an angiogenic hydrogel that was characterized in vitro and in vivo. Such compounds can be triggered with a polymeric substance, such as an HSGAG, to self-assemble from solution into a gel. Biologically, an HBPA-heparin/heparan gel, representative of other compositions and configurational matrices of this invention, has the unique ability to induce endothelial cells to form highly organized capillary-like tubules with continuous lumen in three dimensions in culture and most important of inducing ischemic wound healing without exogenous growth factors.

EXAMPLES OF THE INVENTION

The following non-limiting examples and data illustrate various aspects and features relating to the amphiphile compounds, nanofibers, gels, compositions and/or methods of the present invention, including the self-assembly of heparin-binding peptide amphiphiles and corresponding delivery of heparin, heparan and/or related growth factors, as are available through the methodologies described herein. In comparison with the prior art, the present methods, compounds and compositions provide results and data which are surprising, unexpected and contrary thereto. While the utility of this invention is illustrated through the use of several amphiphilic compounds and components thereof, it will be understood by those skilled in the art that comparable results are obtainable with various other amphiphile compounds and/or components, as are commensurate with the scope of this invention.

Example 1

HBPA gel formation. All reagents were purchased from Fisher and used as received unless otherwise specified. HBPAs were synthesized using methods described in the aforementioned incorporated references. Various other amphiphilic peptide compositions, in accordance with this invention, comprising other residues and/or hydrophobic components can be prepared as also described therein. Briefly, the peptide was constructed on a Rink amide resin using an automated solid phase peptide synthesizer (Applied Biosystems-733A) with appropriately protected amino acids (Novabiochem) for standard fluorenylmethoxycarbonyl (Fmoc) chemistry. The N-terminus of the peptide was capped with palmitic acid using an alkylation reaction, followed by deprotection and cleavage of the HBPA from the resin using trifluoracetic acid (TFA), water and trisiopropylsilane. TFA was removed by rotary evaporation and triturated the HBPA product using cold diethyl ether, which was then filtered and vacuum dried. The molecular weight of the HBPA was characterized by electrospray ionization mass spectrometry. The HBPA was solubilized in 1 M hydrochloric acid at room temperature for one hour and then subsequently lyophilized it to decrease the residual TFA counter ions and replace them with chloride ions. The HBPA was resolubilized at 30 mg/mL at pH 7.4 (unless otherwise specified) in de-ionized water using 1 M sodium hydroxide as needed. The HBPA gels were formed by mixing equal volumes of the HBPA solution made as above and the gel trigger—either heparin sodium or heparan sodium Sigma) in concentrations of 20 mg/mL (to obtain a stoichiometry of 1:1.84 for HBPA: heparin/heparan) or disodium hydrogen phosphate in solution in concentration of 11 mg/ml—to obtain a final product of 1.5 w/v % HBPA gels. Whenever lower weight percent gels were made, the heparin, heparan and the phosphate were scaled down appropriately to maintain the stoichiometry.

Example 2

Characterization of the self-assembly. Heparin-gold stained HBPA samples were prepared for transmission electron microscopy (TEM) as previously described. (Sanantonio, J. D., A. D. Lander, M. J. Karnovsky and H. S. Slayter; "Mapping the heparin-binding sites on type-I collagen monomers and fibrils." *Journal of Cell Biology* 125, (1994) 1179-1188.) Briefly, a holey carbon coated copper grid was dipped twice in solutions of HBPA-1 (0.1 w/v % in water) for 20 s, stained with colloidal 10 nm gold-tagged heparin-albumin solution diluted 1:20 in the recommended buffer (Sigma) for 30 min. at 4° C., fixed in 4 v/v % formaldehyde (Sigma) in phosphate buffered saline (PBS-Gibco) at room temperature for 20 min. and then counter-stained in 2 w/v % uranyl acetate for 45 minutes at room temperature with two washes in 0.1 M cacodylate buffer with 0.5 w/v % bovine serum albumin and 0.05 v/v % Tween 20 between steps (Sigma). In the case of HBPA-2, a holey carbon coated copper grid was dipped twice in a 1% HBPA-2-heparin gel suspension for 20 s and then stained in phosphotungstic acid (Sigma) at room temperature. TEM was performed on a Hitachi 8100 microscope at an accelerating voltage of 200 kV. Confocal fluorescent microscopy was performed by mixing 10 μL each of a 0.04 w/v % HBPA-1 in water solution and 0.03 w/v % in water of fluorescein-heparin (Sigma) solution and imaging with a Leica laser confocal scanning microscope (DM IRE2). The images were analyzed using the Leica LCS imaging software. A Paar Physica MCR300 rheometer with a stainless steel parallel plate of 20 mm was used to perform oscillating rheology experiments on gels prepared in situ by mixing 80 μL 2 w/v % HBPAs in water and either 1 mg of heparin or 0.5 mg of disodium hydrogen phosphate in 80 μL of water or adding 80 μL of 0.25 M NaOH and maintained temperature at 22° C. A frequency sweep experiment was performed at 3% strain with a ten-minute wait time (both determined by independently performing an amplitude sweep and a time strain experiment) to obtain 17 data points between angular frequencies of 0.1 to 10 rad/s. CD spectra were collected, on a Jasco J-715 CD spectrometer using a 0.1 cm path length quartz cuvette, from four samples: blank control, 0.105 mg of HBPA-1 or HBPA-2, 0.07 mg of heparin and a mix of 0.105 mg of the two HBPAs separately and 0.07 mg heparin each in 350 μL of water at pH 7. Isothermal calorimetry (Microcal-ITC) was performed by titrating heparin in 4 μL aliquots from a stock solution of 101.5 μg/mL solution into a 40.1 μg/ml HBPA-1 or -2 solution (all solutions in water). The same amount of heparin was titrated into a blank solution to obtain background values. The raw data was obtained in terms of the heat released by the binding between the two versus their molar ratio to the data was integrated and fit to a curve for a single type of binding site to obtain a binding constant as described previously, referenced above.

Example 3

Release profile of FGF-2 from HBPA-1-heparin gel. FGF-2 (Peprotech) was covalently linked to N-hydroxysuccinimide-rhodamine by means of an ester linkage using a commercially available rhodamine protein labeling kit (Pierce Biotechnology), adding 12.5 ng of this FGF-2 rhodamine to a 100 μl solution of either 20 mg/ml heparin in water or 11 mg/ml disodium hydrogen phosphate. These solutions were added to a 100 μl solution of 3 w/v % HBPA-1 solution in water to respectively obtain HBPA-1-heparin or HBPA-1-phosphate gels with FGF-2 rhodamine. The gels were covered with 100 μl water and incubated at 37° C. in an incubator (5% $CO_2$) and changed initially at 5 minutes and then subsequently every day for 10 days. The changed water was collected and analyzed using a Gemini EM fluorescence plate reader (ex/em maxima 544/576 nm). The fluorescence of an aliquot of the original FGF-2 in heparin or phosphate solution was measured and this value was used to obtain the percentage released.

Example 4

In-vitro angiogenesis assay. PAEC were grown to passage 14 or 15 in phenol red free Dulbecco's modified Eagle medium with 20% v/v fetal bovine serum, 1% v/v penicillin-streptomycin, 2% v/v L-glutamine and 1 mM each of sodium pyruvate and modified Eagle medium amino acids (the serum was obtained from Hyclone while the media and other additives from Gibco). The freeze media was made by adding 5 v/v % dimethyl sulfoxide (Sigma) to the above media. The cells were grown in cell culture incubators at 37 C with 5% $CO_2$. The sandwich gels were made in 8-well chambered cover slip (Nalge Nunc) containers. The first layer of the HBPA-heparin gels was created by mixing 100 μl of 30 mg/ml of HBPA-1 or -2 in water at pH 7 with 100 μl of 20 mg/ml heparin in the above cell culture media with or without 12.5 ng each (to give a total concentration in the well of 31.25 ng/ml) of FGF-2 and VEGF (both from Peprotech). 200 μl 3 w/v % collagen gels were made using type I rat tail collagen (Roche), which was gelled in a base chamber and then equilibrated with the above media to obtain a pH of 7.4. The gel was allowed to set by leaving it at room temperature overnight. Subsequently, 750,000 bPAECs per well were plated in culture media and followed up with alternate day media changes in the incubator until cells grew to confluence through the thickness of the gel (usually by day 5). Excess media was removed and the second layer of gel was added on top of the cell layer exactly as before. The collagen gels were made in a separate 8 well chamber slide and then placed on top of the cell layer after pH equilibration as before. After a half hour wait at room temperature, media was added and the wells were incubated at 37 C and then changed media every alternate day. Supplemental heparin was added with or without the growth factors at the same concentrations as above to the specifically defined collagen gel controls. We did not supplement either kind of the HBPA-heparin gels with heparin or growth factors in the media. Hence the only source of supplemental growth factors for both the HBPA-heparin gels with growth factors was from the two gel layers. The cell cultures were observed daily using light microscopy. At day 7, the cells were stained with a fluorescein-based cell tracer (Vybrant CFDA SE cell tracer-Molecular Probes) at 20 μM concentration and imaged them using a Leica laser confocal scanning microscope (DM IRE2) to obtain a z-series through the gels. Volocity and NIH ImageJ software were used for 3-D rendering of the z-series images.

Example 5

Rabbit ear ischemic wound healing assay. An assay was used to measure the ability of the matrix to induce wound healing in an ischemic area (Ahn S T, Mustoe T A. "Effects of ischemia on ulcer wound healing: a new model in the rabbit ear." *Ann Plast Surg.* 24 (1990) 17-23)). Protocols were approved by Northwestern's Animal Care and Usage Committee. Animals were anesthetized with ketamine and xylazine and a sterile surgical incision was made 1 cm distal to the root of the ear. The central and rostral arteries were identified, ligated with 4-0 ethilon and interrupted taking care to leave the respective veins untouched. The incision was extended circumferentially around the base of the ear interrupting dermal circulation leaving the small caudal artery as the only source of blood supply to the ears and then sutured close. On the ventral surface, a 6 mm biopsy punch was used to create four circular wounds upto and including the perichondrium leaving the bare cartilage as the wound base. The necessary materials were applied with the HBPA-heparan being gelled in situ where specified. The wounds were covered with a thin polyurethane wound dressing (Tegaderm™) and animals were given appropriate post-operative analgesia. The animals were housed for twelve days in the appropriate facility. At the end of twelve days, they were anesthetized and then euthanized with intra cardiac Euthasol™ followed by surgical induction of pneumothorax to confirm euthanasia. The wounds were harvested with a 1 mm cuff of normal tissue using a 7 mm biopsy punch going through to the dorsal skin. These wounds were placed in buffered formalin, fixed, paraffin embedded and stained by Masson's trichrome after bisecting. The gap between the leading edge of the epithelium was measured in each wound in order to quantify wound healing with a measurement of zero indicating complete healing. The results were aggregated and statistically analyzed using a two sample t test assuming unequal variances.

While the principals of this invention have been described in connection with specific embodiments, it should be understood clearly that these descriptions are added only by way of example and are not intended to limit, in any way, the scope of this invention. For instance, certain embodiments have been described as providing a compositional matrix that can bind and control delivery of certain angiogenic growth factors to promote capillary-like structures with a degree of endothelial cell organization not previously reported. However, such a vascularizing matrix can also be used for the controlled delivery and release of various other growth factors. Likewise, such a composition or matrix can be formed in situ upon introduction or injection of liquid precursor compounds or components into a cellular medium.

We claim:

1. A synthetic amphiphilic peptide compound consisting of X-Y-AAAAGGGLRKKLGKA (SEQ ID NO:3) where X is an alkyl moiety ranging from about six carbon residues to about twenty-two carbon residues and Y is C=O.

2. The compound of claim 1 wherein residues of the peptide component are capable of interacting with a sulfated glycosaminoglycan selected from heparin, heparan sulfate and combinations thereof.

3. The compound of claim 1 wherein said peptide amphiphilic compound consists of H3C(CH2)14CO-AAAAGGGLRKKLGKA (SEQ ID NO:3).

4. The compound of claim 2 in composition with a sulfated polysaccharide, said composition comprising a micellar configuration.

5. The compound of claim 4, wherein said polysaccharide is a sulfated glycosaminoglycan selected from heparin, heparan sulfate and combinations thereof.

6. The compound of claim 5, said composition capable of interacting with an angiogenic growth factor.

7. The compound of claim 6, said growth factor selected from a heparin binding growth factor, a heparan binding growth factor and combinations thereof.

8. A composition comprising a sulfated polysaccharide and an amphiphilic peptide compound wherein the amphiphilic peptide compound consists of X-Y-AAAAGGGL-RKKLGKA (SEQ ID NO:3) where X is an alkyl moiety ranging from about six carbon residues to about twenty-two carbon residues and Y is C=O, said composition comprising a micellar configuration.

9. The composition of claim 8 wherein said polysaccharide is a sulfated glycosaminoglycan selected from heparin, heparan sulfate and combinations thereof.

10. The composition of claim 8 wherein said peptide amphiphile compound is consists of H3C(CH2)144CO-AAAAGGGLRKKLGKA (SEQ ID NO:3).

11. The composition of claim 10 comprising an angiogenic growth factor selected from a heparin binding growth factor, a heparan binding growth factor and combinations thereof.

12. The composition of claim 11 wherein said factor is selected from vascular endothelial growth factor (VEGF) and fibroblast growth factor-2 (FGF-2).

* * * * *

UNITED STATES PATENT AND TRADEMARK OFFICE
CERTIFICATE OF CORRECTION

PATENT NO. : 7,851,445 B2
APPLICATION NO. : 11/368582
DATED : December 14, 2010
INVENTOR(S) : Samuel I. Stupp et al.

It is certified that error appears in the above-identified patent and that said Letters Patent is hereby corrected as shown below:

In Claim 10 in column 18, line 2, please change "H3C(CH2)144CO" to --H3C(CH2)14CO--.

Signed and Sealed this
Twenty-seventh Day of November, 2012

David J. Kappos
*Director of the United States Patent and Trademark Office*

SEQUENCE LISTING

```
<160> NUMBER OF SEQ ID NOS: 5

<210> SEQ ID NO 1
<211> LENGTH: 8
<212> TYPE: PRT
<213> ORGANISM: Artificial Sequence
```

```
<220> FEATURE:
<223> OTHER INFORMATION: Synthesized Peptides

<400> SEQUENCE: 1

Leu Arg Lys Lys Leu Gly Leu Ala
1               5

<210> SEQ ID NO 2
<211> LENGTH: 8
<212> TYPE: PRT
<213> ORGANISM: Artificial Sequence
<220> FEATURE:
<223> OTHER INFORMATION: Synthesized Peptides

<400> SEQUENCE: 2

Leu Leu Gly Ala Arg Lys Lys Lys
1               5

<210> SEQ ID NO 3
<211> LENGTH: 15
<212> TYPE: PRT
<213> ORGANISM: Artificial Sequence
<220> FEATURE:
<223> OTHER INFORMATION: Synthesized Peptides

<400> SEQUENCE: 3

Ala Ala Ala Ala Gly Gly Gly Leu Arg Lys Lys Leu Gly Lys Ala
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: Synthesized Peptides

<400> SEQUENCE: 4

Ala Ala Ala Ala Gly Gly Gly Leu Leu Gly Ala Arg Lys Lys Lys
1               5                   10                  15

<210> SEQ ID NO 5
<211> LENGTH: 5
<212> TYPE: PRT
<213> ORGANISM: Artificial Sequence
<220> FEATURE:
<223> OTHER INFORMATION: Synthetic Peptides

<400> SEQUENCE: 5

Ile Lys Val Ala Val
1               5
```